US012698324B2

(12) United States Patent
Yamamoto et al.

(10) Patent No.: US 12,698,324 B2
(45) Date of Patent: Aug. 4, 2026

(54) CYSTIC LYMPHANGIOMA TREATMENT DRUG

(71) Applicant: National University Corporation University of Toyama, Toyama (JP)

(72) Inventors: Seiji Yamamoto, Toyama (JP); Masakiyo Sasahara, Toyama (JP); Takeru Hamashima, Toyama (JP); Noriko Okuno, Toyama (JP)

(73) Assignee: NATIONAL UNIVERSITY CORPORATION UNIVERSITY OF TOYAMA, Toyama (JP)

( * ) Notice: Subject to any disclaimer, the term of this patent is extended or adjusted under 35 U.S.C. 154(b) by 511 days.

(21) Appl. No.: 18/020,449

(22) PCT Filed: Nov. 24, 2021

(86) PCT No.: PCT/JP2021/042867
§ 371 (c)(1),
(2) Date: Feb. 9, 2023

(87) PCT Pub. No.: WO2022/118696
PCT Pub. Date: Jun. 9, 2022

(65) Prior Publication Data
US 2023/0295286 A1 Sep. 21, 2023

(30) Foreign Application Priority Data

Dec. 4, 2020 (JP) ................................. 2020-201580
Apr. 13, 2021 (JP) ................................. 2021-067500

(51) Int. Cl.
C07K 16/22 (2006.01)
A61P 35/00 (2006.01)
C12N 15/113 (2010.01)
C12N 15/115 (2010.01)

(52) U.S. Cl.
CPC .............. *C07K 16/22* (2013.01); *A61P 35/00* (2018.01); *C12N 15/1136* (2013.01); *C12N 15/115* (2013.01); *C12N 2310/11* (2013.01); *C12N 2310/14* (2013.01); *C12N 2310/16* (2013.01)

(58) Field of Classification Search
CPC ................................ C07K 16/22; A61P 35/00
See application file for complete search history.

(56) References Cited

U.S. PATENT DOCUMENTS

2019/0113513 A1    4/2019    Shaked
2020/0316173 A1    10/2020   Shaked

FOREIGN PATENT DOCUMENTS

CA          2 568 427        1/2006
JP          2007/523599 A    8/2007

OTHER PUBLICATIONS

Berasain et al.—Amphiregulin. Semin. Cell Develop. Biology, 28, 31-41, 2014. (Year: 2014).*
Bade et al., Mammary tumorigenesis induced by fibroblast growth factor receptor 1 requires activation of the epidermal growth factor receptor. J. Cell Sci. 124, 3106-3117, 2011. (Year: 2011).*
R&D Systems. AF989 data sheet. AccessedOct. 28, 2025 (Year: 2025).*
FDA. Erlotinib (TARCEVA®) data sheet. Apr. 2010. (Year: 2010).*
Gore et al "Combined Targeting of TGF-β, EGFR and HER2 Suppresses Lymphangiogenesis and Metastasis in a Pancreatic Cancer Model" Cancer Letters vol. 379, pp. 143-153, 2016.
Marino et al "Activation of the Epidermal Growth Factor Receptor Promotes Lymphangiogenesis in the Skin" Journal of Dermatological Science vol. 71, pp. 184-194, 2013.
Yamamoto et al "Analysis of the Molecular Mechanism of Exacerbation of Human Cystic Lymphangioma" The 110th Annual Meeting of the Japanese Society of Pathology, p. 247, Mar. 15, 2021.
Yamamoto "PDGFRβ Knockout Fibroblasts are Involved in the Formation of Cyst-Like Lymphatic Vessels" The 109th Annual Meeting of the Japanese Society of Pathology, p. 332, Mar. 2, 2020.
Yoshida et al "Dysregulation of Amphiregulin Stimulates the Pathogenesis of Cystic Lymphangioma" PNAS vol. 118, pp. 1-9, May 11, 2021.
Yamamoto et al., "3-H-06 PDGFR β knockout fibroblasts are involved in the formation of cyst-like lymphatic vessels", Proceeding of the Japanese Society of Pathology, 2020, vol. 109, No. 1, p. 332, with partial English-language translation.
Extended European Search Report issued Oct. 4, 2024 in corresponding European Patent Application No. 21900451.2.

* cited by examiner

*Primary Examiner* — Elly-Gerald Stoica
(74) *Attorney, Agent, or Firm* — Wenderoth, Lind & Ponack, L.L.P.

(57) ABSTRACT

A pharmaceutical composition for preventing or treating cystic lymphangioma comprising an agent that causes suppression of expression of amphiregulin, suppression of secretion of amphiregulin, and/or inhibition of binding of amphiregulin with an amphiregulin receptor, or an agent that causes suppression of expression of an amphiregulin receptor, suppression of activation of an amphiregulin receptor, and/or inhibition of binding of an amphiregulin receptor with amphiregulin, as an active ingredient.

5 Claims, 3 Drawing Sheets
Specification includes a Sequence Listing.

Fig. 1
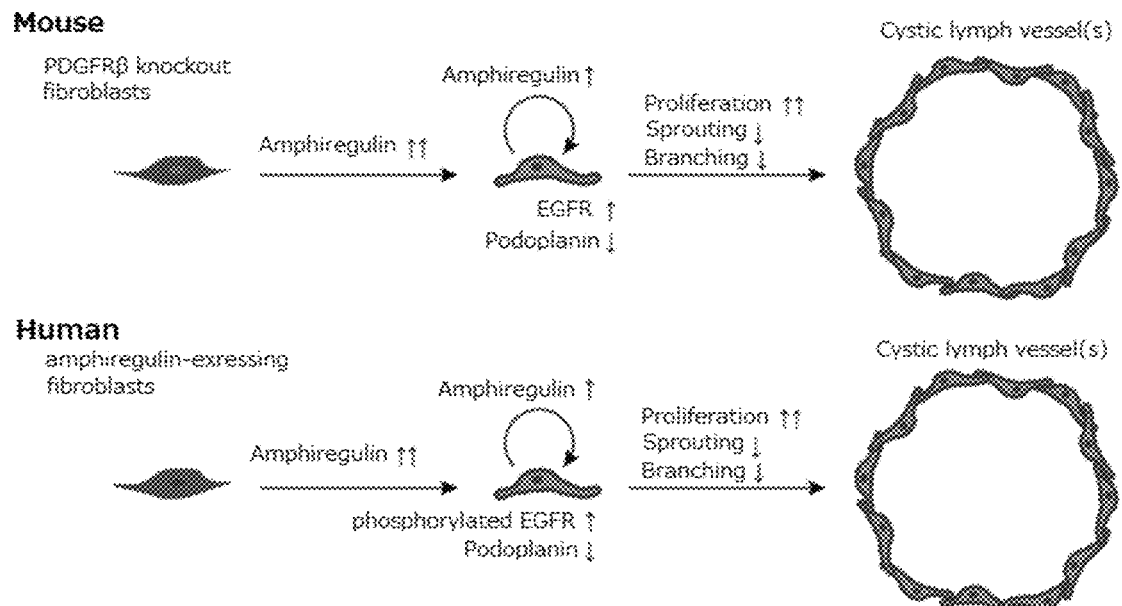
Fig. 2A
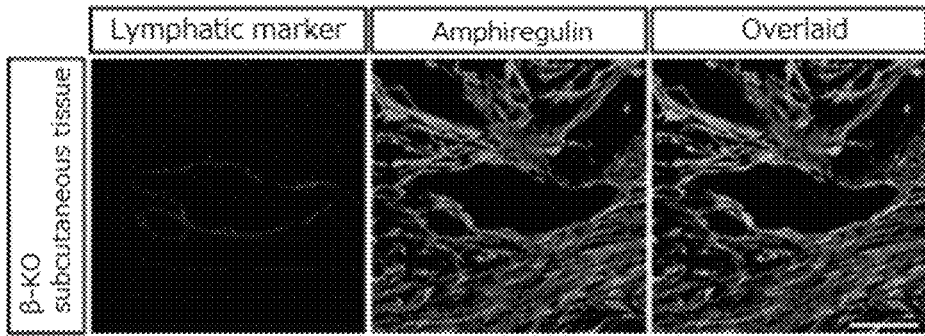
Fig. 2B

Amphiregulin
in fibroblasts

CYSTIC LYMPHANGIOMA TREATMENT DRUG

CROSS-REFERENCE TO RELATED APPLICATIONS

This application is the national stage of International Patent Application No. PCT/JP2021/042867, filed on Nov. 24, 2021, which claims priority to Japanese Patent Application No. 2020-201,580, filed on Dec. 4, 2020, and Japanese Patent Application No. 2021-067,500, filed on Apr. 13, 2021, the entire contents of which are hereby incorporated by reference in their entirety.

SEQUENCE LISTING

A computer readable file containing a sequence listing is being electronically co-filed herewith via EFS-Web. The computer readable file, submitted under 37 CFR § 1.821(e), will also serve as the copy required by 37 § CFR 1.821(c). The file (filename "40Y0986.TXT") was created on Feb. 7, 2023 and has a size of 120,521 bytes. The content of the computer readable file is hereby incorporated by reference in its entirety.

TECHNICAL FIELD

The present invention relates to a medicinal drug for cystic lymphangioma. More particularly, the present invention relates to a pharmaceutical composition and a kit for preventing or treating cystic lymphangioma, a method for testing cystic lymphangioma, a test kit for cystic lymphangioma, and a test agent for cystic lymphangioma.

BACKGROUND ART

Cystic lymphangioma is characterized by incidence of giant cysts. It has good outcomes from surgical resection. However, there are some cases in which cysts are unresectable, with the resection depending on the site of occurrence, such as a site adjacent to a child's respiratory tract and a site near an eye, nose, or mouth, and also in some cases, the treatment effect of sclerotherapy is insufficient. The development of a therapeutic agent for cystic lymphangioma based on molecular mechanisms has been desired.

PTL 1 discloses ligands for a protein associated with regulation of obesity, diabetes, and metabolic energy levels in animals, including humans. However, hundreds of diseases, including Alzheimer's disease and diabetes, are listed, and cystic lymphangioma is merely one of them. In addition, no substance associated with prevention or treatment of cystic lymphangioma is described.

CITATION LIST

Patent Literature

PTL 1
Japanese Patent Publication No. 2007-523599

SUMMARY OF INVENTION

Technical Problem

A problem to be solved by the present invention is to provide a pharmaceutical composition and a kit for preventing or treating cystic lymphangioma comprising an agent that had not been reported as an active ingredient, a method for testing cystic lymphangioma, a test kit for cystic lymphangioma, and a test agent for cystic lymphangioma.

Solution to Problem

The present invention covers the following embodiments.

Item 1. A pharmaceutical composition for preventing or treating cystic lymphangioma comprising an agent that causes suppression of expression of amphiregulin, suppression of secretion of amphiregulin, and/or inhibition of binding of amphiregulin with an amphiregulin receptor, as an active agent.

Item 2. The pharmaceutical composition according to Item 1, wherein the agent is selected from the group consisting of a neutralizing antibody against amphiregulin, an antigen binding fragment of a neutralizing antibody against amphiregulin, an antisense oligonucleotide against amphiregulin, a small interfering RNA against amphiregulin, a ribozyme against amphiregulin, and an aptamer against amphiregulin.

Item 3. A pharmaceutical composition for preventing or treating cystic lymphangioma comprising an agent that causes suppression of expression of an amphiregulin receptor, suppression of activation of an amphiregulin receptor, and/or inhibition of binding of an amphiregulin receptor with amphiregulin, as an active ingredient.

Item 4. The pharmaceutical composition according to Item 3, wherein the agent is selected from the group consisting of a neutralizing antibody against an amphiregulin receptor, an antigen binding fragment of a neutralizing antibody against an amphiregulin receptor, an antisense oligonucleotide against an amphiregulin receptor, a small interfering RNA against an amphiregulin receptor, a ribozyme against an amphiregulin receptor, an aptamer against an amphiregulin receptor, and a low-molecular compound that inhibits proliferation of lymphatic endothelial cells via an amphiregulin receptor.

Item 5. Use of an agent of either (a) or (b) for manufacturing a medicament for preventing or treating cystic lymphangioma:
(a) an agent that causes suppression of expression of amphiregulin, suppression of secretion of amphiregulin, and/or inhibition of binding of amphiregulin with an amphiregulin receptor; and
(b) an agent that causes suppression of expression of an amphiregulin receptor, suppression of activation of an amphiregulin receptor, and/or inhibition of binding of an amphiregulin receptor with amphiregulin.

Item 6. A medicament for inhibiting proliferation of lymphatic endothelial cells comprising an agent of either (a) or (b) as an active ingredient:
(a) an agent that causes suppression of expression of amphiregulin, suppression of secretion of amphiregulin, and/or inhibition of binding of amphiregulin with an amphiregulin receptor; and
(b) an agent that causes suppression of expression of an amphiregulin receptor, suppression of activation of an amphiregulin receptor, and/or inhibition of binding of an amphiregulin receptor with amphiregulin.

Item 7. A kit for preventing or treating cystic lymphangioma comprising an agent of either (a) or (b):
(a) an agent that causes suppression of expression of amphiregulin, suppression of secretion of amphiregulin, and/or inhibition of binding of amphiregulin with an amphiregulin receptor; and (b) an agent that causes suppression of expression of an amphiregulin receptor, suppression of activation of an amphiregulin receptor, and/or inhibition of binding of an amphiregulin receptor with amphiregulin.

Item 8. A method for testing cystic lymphangioma comprising measuring amphiregulin or an amphiregulin receptor in a sample collected from a subject.

Item 9. A test kit for cystic lymphangioma comprising either (a) or (b):

(a) a substance that binds amphiregulin selected from the group consisting of a neutralizing antibody against amphiregulin, an antigen binding fragment of a neutralizing antibody against amphiregulin and an aptamer against amphiregulin, a substance that binds DNA encoding amphiregulin, a substance that binds mRNA transcribed based on DNA encoding amphiregulin as a template, and cDNA reverse-transcribed based on amphiregulin mRNA as a template; and (b) a substance that binds an amphiregulin receptor selected from the group consisting of a neutralizing antibody against an amphiregulin receptor, an antigen binding fragment of a neutralizing antibody against an amphiregulin receptor and an aptamer against an amphiregulin receptor, a substance that binds DNA encoding an amphiregulin receptor, a substance that binds mRNA transcribed based on DNA encoding an amphiregulin receptor as a template, and cDNA reverse-transcribed based on amphiregulin receptor mRNA as a template.

Item 10. A test agent for cystic lymphangioma comprising either substance (a) or (b):

(a) a substance that binds amphiregulin selected from the group consisting of a neutralizing antibody against amphiregulin, an antigen binding fragment of a neutralizing antibody against amphiregulin and an aptamer against amphiregulin, a substance that binds DNA encoding amphiregulin, a substance that binds mRNA transcribed based on DNA encoding amphiregulin as a template, and cDNA reverse-transcribed based on amphiregulin mRNA as a template; and (b) a substance that binds an amphiregulin receptor selected from the group consisting of a neutralizing antibody against an amphiregulin receptor, an antigen binding fragment of a neutralizing antibody against an amphiregulin receptor and an aptamer against an amphiregulin receptor, a substance that binds DNA encoding an amphiregulin receptor, a substance that binds mRNA transcribed based on DNA encoding an amphiregulin receptor as a template, and cDNA reverse-transcribed based on amphiregulin receptor mRNA as a template.

Advantageous Effects of Invention

According to the invention, an agent that is effective for preventing and/or treating cystic lymphangioma, for which there has been no basic therapeutic agent, is provided.

BRIEF DESCRIPTION OF DRAWINGS

FIG. 1 is a schematic view of molecular mechanisms of the formation of cystic abnormal lymph vessels in a mouse and human.

FIG. 2A is immunohistological staining around lymphangioma of a PDGFRβ knockout mouse. Left: lymphatic marker (LYVE1); middle: amphiregulin; right: an overlaid image of lymphatic marker (LYVE1), amphiregulin, and nucleus. The scale bar is 50 μm.

FIG. 2B is western-blot analysis of expression of amphiregulin in fibroblasts. Flox: control group; (β-KO: a group of tamoxifen-administered PDGFRβ knockout mice. * is <0.05.

DESCRIPTION OF EMBODIMENTS

Figure 3A:
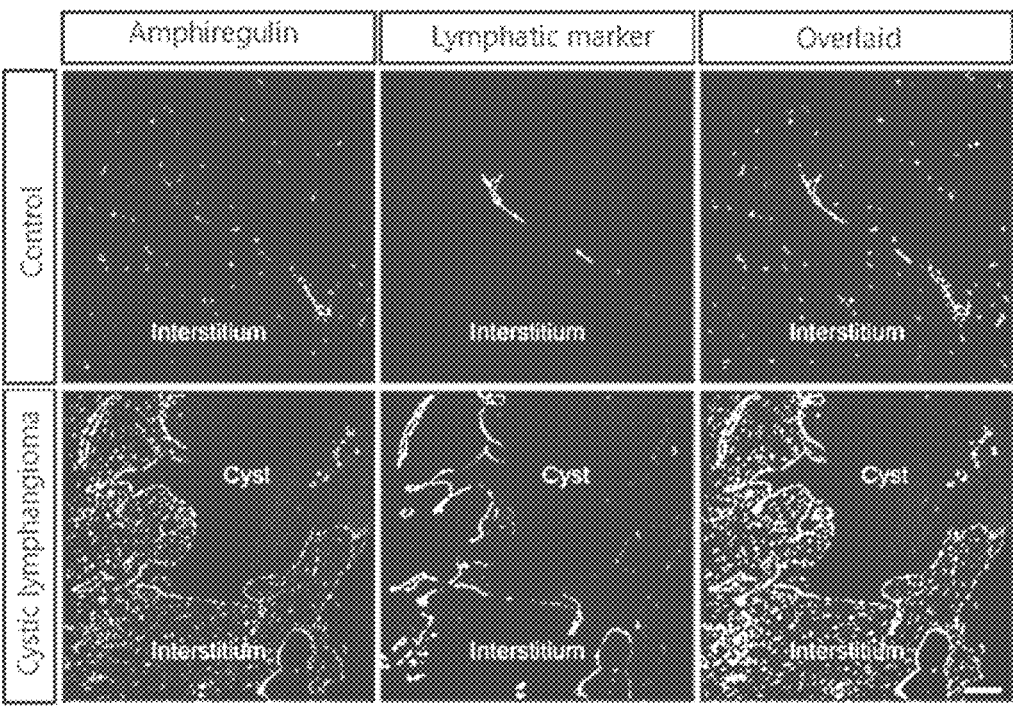
FIG. 3A is immunohistological staining of a lesional tissue of lymph vessels derived from a patient with human cystic lymphangioma. Left: amphiregulin; middle: lymphatic marker (podoplanin); right: an overlaid image of amphiregulin, lymphatic marker (podoplanin), and nucleus. The scale bar is 100 μm.

As used herein, the term "a subject" refers to a mammal, including a human, mouse, rat, bovine, horse, pig, dog, cat, rabbit, goat, and sheep. Preferably, the subject is a human or mouse. More preferably, the subject is a human.

As used herein, the term "treatment" refers to a cure or improvement of a disease or symptom, or suppression of a symptom. The term "prevention" refers to prevention of onset of a disease or symptom.

To develop a new drug, an animal model that reflects the clinical condition of a human is required. For cystic lymphangioma, mice having dilation of lymph vessels have been known to some extent. However, most of them are inappropriate as an animal model of human lymphangioma because anastomosis between a blood vessel and lymph vessel, such as dysfunction of blood platelets, occurs in the course of development and secondarily causes dilation of lymph vessels.

Recently, we developed a model of lymphangiogenesis in adult mice. By applying this model to uniquely produced PDGFRβ-conditioned systemic knockout mice (denoted as "PDGFRβ knockout mice" hereinafter) (Stem Cells, 2016 March; 34(3): 685-98. doi: 10.1002/stem.2212; EBioMedicine, 2018 May; 31: 190-201. doi: 10.1016/j.ebiom.2018.04.021.), cystic lymphangioma-like clinical conditions were successfully regenerated.

After searching for a factor of dilation of lymphatic vessels using the above mice, the inventors surprisingly found that amphiregulin, which had so far not attracted attention, was highly expressed in fibroblast cells around a lesional site. The invention was thus achieved.

According to a first aspect of the invention, provided is a pharmaceutical composition for preventing or treating cystic lymphangioma comprising an agent that causes suppression of expression of amphiregulin, suppression of secretion of amphiregulin, and/or inhibition of binding of amphiregulin with an amphiregulin receptor, as an active agent.

Secretion of amphiregulin indicates secretion of amphiregulin in secretory form to outside the cells (e.g., release from a cell membrane in a shedding manner).

Amphiregulin (AREG) is a glycoprotein that is a member of the epidermal growth factors (EGF) and has an action to promote growth of epidermal cells by interacting with an EGF receptor Amphiregulin includes membrane-bound amphiregulin (also referred to as "amphiregulin proprotein" or "amphiregulin preproprotein") and secretory amphiregulin (also referred to as "amphiregulin protein"). For these amphiregulins, see Semin, Cell Dev Biol 2014 April; 28: 31-41. doi: 10.1016/j.semcdb.2014.01.005.

In one embodiment, amphiregulin is a protein having an amino acid sequence that is at least 90% identical to the amino acid sequence represented by SEQ ID NO. 1, 2, 3, 4, 5, or 6.

SEQ ID NO. 1 is an amino acid sequence of human membrane-bound amphiregulin protein consisting of 252 amino acids (GenBank Accession Number: NP_001648.1). SEQ ID NO. 2 is human secretory amphiregulin protein and corresponds to a portion of the $101^{th}$ to $187^{th}$ amino acids in the amino acid sequence of human membrane-bound amphiregulin protein.

SEQ ID NO. 3 is an amino acid sequence of mouse membrane-bound amphiregulin protein consisting of 248 amino acids (GenBank Accession Number: NP_033834.1). SEQ ID NO. 4 is mouse secretory amphiregulin protein and corresponds to a portion of the $100^{th}$ to $180^{th}$ amino acids in the amino acid sequence of mouse membrane-bound amphiregulin protein.

SEQ ID NO. 5 is an amino acid sequence of rat membrane-bound amphiregulin protein consisting of 243 amino acids (GenBank Accession Number: NP 058819.1). SEQ ID NO. 6 is rat secretory amphiregulin protein and corresponds to a portion of $97^{th}$ to $178^{th}$ amino acids in the amino acid sequence of rat membrane-bound amphiregulin protein.

In more preferred embodiments, amphiregulin is a protein having an amino acid sequence that is at least 95% identical, at least 98% identical, at least 99% identical, or 100% identical to the amino acid sequence represented by SEQ ID NO. 1, 2, 3, 4, 5, or 6.

In more preferred embodiments, amphiregulin is a protein having an amino acid sequence that is at least 90% identical, at least 95% identical, at least 98% identical, at least 99% identical, or 100% identical to the amino acid sequence represented by SEQ ID NO. 1 or SEQ ID NO. 2, and having an action to promote proliferation of cells that express EGFR and HER2, or cells that express EGFR but do not express HER2.

In more preferred embodiments, amphiregulin is a protein having an amino acid sequence that is at least 90% identical, at least 95% identical, at least 98% identical, at least 99% identical, or 100% identical to the amino acid sequence represented by SEQ ID NO. 3 or SEQ ID NO. 4, and having an action to promote proliferation of cells that express EGFR and HER2, or cells that express EGFR but do not express HER2.

FIG. 1 shows molecular mechanisms of the formation of cystic abnormal lymph vessels in a mouse and human. On the upper side of FIG. 1, the upward arrows indicate an increase in the expression amount of molecules in fibroblasts around lymph vessels of PDGFRβ knockout mouse fibroblasts or an increase in the expression of molecules or an increase in proliferation activity of lymphatic endothelial cells, compared with fibroblasts around lymph vessels of a normal mouse. The downward arrows indicate a decrease in the expression amount of molecules in lymphatic endothelial cells or a decrease in sprouting or branching of lymph vessels. On the lower side of FIG. 1, the upward arrows indicate an increase in the expression amount of molecules in fibroblasts around lymph vessels of patients with cystic lymphangioma or an increase in the expression of molecules or an increase in phosphorylated proteins, compared with fibroblasts around lymph vessels of a normal human. The downward arrows indicate a decrease in an expression amount of molecules in lymphatic endothelial cells or a decrease in sprouting or branching of lymph vessels.

Without wishing to be bound by any specific hypothesis or theory, according to the present studies of the inventors, it was revealed that amphiregulin was excessively secreted from fibroblast cells around lymph vessels in PDGFRβ knockout mice, which induces secretion of amphiregulin from lymphatic endothelial cells and excessive proliferation of lymphatic endothelial cells. It was also revealed that, also in human cystic lymphangioma, amphiregulin was excessively secreted from fibroblast cells around lymph vessels, which induces secretion of amphiregulin from lymphatic endothelial cells and excessive proliferation of lymphatic endothelial cells. This is the molecular mechanism of onset and exacerbation of cystic lymphangioma.

In some embodiments, the agent that causes suppression of expression of amphiregulin, suppression of secretion of amphiregulin, and/or inhibition of binding of amphiregulin with an amphiregulin receptor is selected from the group consisting of a neutralizing antibody against amphiregulin, an antigen binding fragment of a neutralizing antibody against amphiregulin, an antisense oligonucleotide against amphiregulin, a small interfering RNA against amphiregulin, a ribozyme against amphiregulin, and an aptamer against amphiregulin. Containing one or more such agents as an active ingredient is effective for the prevention or treatment of cystic lymphangioma.

Methods for producing an antibody, including a method for producing a neutralizing antibody, are well known. (For example, see Antibodies: A Laboratory Manual (1988) by Ed Harlow and David Lane, Cold Spring Harbor Laboratory Press, Cold Spring Harbor, New York. For antibodies, antibodies according to various embodiments of the invention may be a polyclonal antibody, a monoclonal antibody, a chimeric antibody, a single-stranded antibody, a Fab fragment, and a fragment that is produced with a Fab expression library.)

For the production of an antibody, various hosts, including goats, rabbits, rats, mice, and humans, may be immunized by injection with the polypeptide or any fragment or oligopeptide thereof that has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol.

A monoclonal antibody may be prepared using any technique that provides for the production of antibody molecules by continuous cell lines in culture. It includes, but is not limited to, the hybridoma technique, the human B-cell hybridoma technique, and the EBV-hybridoma technique (essentially as described in Kohler, G. et al. (1975), Nature 256: 495-497; Kozbor, D. et al. (1985), J. Immunol. Methods 81: 31-42; Cote, R. J. et al. (1983), Proc. Natl. Acad. Sci. 80: 2026-2030; Cole, S. P. et al. (1984), Mol. Cell Biol. 62: 109-120).

An antigen binding fragment of a neutralizing antibody means an antigen bonding portion of an antibody molecule and includes any polypeptide (for example, a molecule including one or more CDRs) including Fab, Fab', F(ab')$_2$, Fv, a single-stranded antibody (scFv), a chimeric antibody, a bispecific antibody (diabody), and at least a part of immunoglobulin that is sufficient to provide a specific binding property with an antigen. An antigen binding fragment of a neutralizing antibody can be produced by enzymatic digestion of the antibody molecule. For example, a Fab fragment may be produced by reducing a F(ab')$_2$ fragment that is generated by pepsin digestion of an antibody molecule or disulfide bridges of the F(ab')$_2$ fragment. Alternatively, Fab expression libraries may be constructed to allow rapid and easy identification of monoclonal Fab fragments with the desired specificity (for example as described in Huse, W. D. et al. (1989), Science 254: 1275-1281)$_o$ An antisense oligonucleotide may function as an inhibitor of gene expression of amphiregulin. The antisense oligonucleotide includes an antisense RNA molecule and an antisense DNA molecule. It serves to directly inhibit the translation of amphiregulin mRNA by binding amphiregulin mRNA, thus preventing the translation of amphiregulin into a protein or increasing the degradation of amphiregulin mRNA and then decreasing the expression level (or expression amount) of amphiregulin. For example, an antisense oligonucleotide having at least 15 bases that is complementary to the non-repetitive region of the mRNA transcription sequence encoding amphiregulin may be synthesized by a conventional phosphodiester technique. Methods that are used in an antisense technique for specifically inhibiting gene expression of a gene having a known sequence are well known in the art (for example, see Stein et al. (1988), Nucl. Acids Res. 16). The antisense oligonucleotide may be prepared by known methods such as solid-phase phosphoramidite chemical synthesis. The antisense oligonucleotide may also be generated by transcribing a DNA sequence encoding an RNA molecule in vitro or in vivo. Such a DNA sequence may be incorporated into a wide variety of vectors incorporating an appropriate RNA polymerase promoter such as a T7 or SP6 polymerase promoter.

A small interfering RNA (siRNA) against amphiregulin may also function as an inhibitor of gene expression of amphiregulin. The gene expression of amphiregulin may be decreased by contacting siRNA that is a small double-stranded RNA (dsRNA) or a vector that produces the siRNA with a tissue or cells of a subject. As a result, RNA interference (RNAi) occurs, and gene expression of amphiregulin is specifically inhibited. Methods for selecting an appropriate dsRNA against a gene having a known sequence and an appropriate vector encoding the dsRNA are well known (for example, see Elbashir et al. (2001), Nature AlV. 494-498; Harborth et al. (2003), Antisense Nucleic Acid Drug Dev. 13: 83-106; and Semizarov et al. (2003), Proc Natl Acad Sd USA 100: 6347-635).

A ribozyme may also function as an inhibitor of gene expression of amphiregulin. The ribozyme is an enzymatic RNA molecule that is capable of catalyzing a specific cleavage of RNA. The action mechanism of the ribozyme includes cleavage of the nucleotide strand followed by sequence-specific hybridization of a complementary target RNA and the ribozyme molecule. A ribozyme molecule having a hairpin or hammerhead motif that specifically and efficiently catalyzes cleavage of a nucleotide strand of amphiregulin mRNA is useful in the scope of the invention. A specific ribozyme cleavage site in any potential RNA target can be identified by scanning a target molecule for the ribozyme cleavage sites including the sequences GUA, GUU, and GUC. Once identified, a short RNA having 15 to 20 ribonucleotides corresponding to the region of the target gene including one or more cleavage sites may be evaluated for the predicted structural characterization, such as secondary structure. The ribozyme may be prepared by known methods such as solid-phase phosphoramidite chemical synthesis.

An aptamer is an oligonucleotide that binds the target with high affinity and specificity. An aptamer is a class of molecule that is a replacement of an antibody in molecular recognition. The aptamer against amphiregulin is an oligonucleotide that has the ability to recognize amphiregulin with high affinity and specificity. As is well known in the art, an aptamer may be selected using the SELEX method (systematic evolution of ligands by exponential enrichment).

The agent according to the first aspect of the invention may cause a change in amphiregulin inside and/or outside the cells. For example, the agent may completely or partially inhibit the function of amphiregulin secreted outside the cells. Alternatively, the agent may inhibit the translation of amphiregulin by cleaving or degrading an RNA molecule encoding amphiregulin in cells.

The agents of various embodiments according the first aspect of the invention may control one or more of the following: expression, secretion, localization, and/or activity of a molecule involved in onset or development of cystic lymphangioma upstream or downstream from amphiregulin.

According to a second aspect of the invention, provided is a pharmaceutical composition for preventing or treating cystic lymphangioma comprising an agent that causes suppression of expression of an amphiregulin receptor, suppression of activation of an amphiregulin receptor, and/or inhibition of binding of an amphiregulin receptor with amphiregulin, as an active ingredient.

An amphiregulin receptor includes dimers that consist of two or more molecules of the ErbB family (EGF receptor family) and that receive amphiregulin. The ErbB family includes four receptor-type tyrosine kinases: EGFR (epidermal growth factor receptor, also referred to as "HER1" or "ErbB1"), HER2 (also referred to as "ErbB2"), HER3 (also referred to as "ErbB3"), and HER4 (also referred to as "ErbB4"). Activation of the receptor is caused by phosphorylation of tyrosine residue in the receptor.

In one embodiment, an amphiregulin receptor is a homodimer of proteins each having an amino acid sequence that is at least 90% identical to the amino acid sequence represented by SEQ ID NO. 7, 8, 9, 13, 14, 15, 16, or 17.

SEQ ID NO. 7 is an amino acid sequence of human epidermal growth factor receptor protein consisting of 1,210 amino acids (GenBank Accession Number: NP_005219.2).

SEQ ID NO. 8 is an amino acid sequence of mouse epidermal growth factor receptor protein consisting of 1,210 amino acids (GenBank Accession Number: NP_997538.1).

SEQ ID NO. 9 is an amino acid sequence of rat epidermal growth factor receptor protein consisting of 1,209 amino acids sequence (GenBank Accession Number: ADT91285.1).

SEQ ID NO. 13, 14, 15, 16, and 17 are isoforms of human epidermal growth factor protein of SEQ ID NO. 7 (GenBank Accession Number: NP_001333826.1, NP_001333827.1 NP_ 001333828.1, NP_001333829.1, NP_001333870.1, respectively).

In more preferred embodiments, an amphiregulin receptor is a homodimer of proteins each having an amino acid sequence that is at least 95% identical, at least 98% identical, at least 99% identical, or 100% identical to the amino acid sequence represented by SEQ ID NO. 7, 8, 9, 13, 14, 15, 16, or 17.

In more preferred embodiments, an amphiregulin receptor is a homodimer of proteins each having an amino acid sequence that is at least 90% identical, at least 95% identical, at least 98% identical, at least 99% identical, or 100% identical to the amino acid sequence represented by SEQ ID NO. 7.

In more preferred embodiments, an amphiregulin receptor is a homodimer of proteins each having an amino acid sequence that is at least 90% identical, at least 95% identical, at least 98% identical, at least 99% identical, or 100% identical to the amino acid sequence represented by SEQ ID NO. 8.

In another embodiment, an amphiregulin receptor is a heterodimer of a protein having an amino acid sequence that is at least 90% identical to the amino acid sequence represented by SEQ ID NO. 7, 13, 14, 15, 16, or 17, and a protein having an amino acid sequence that is at least 90% identical to the amino acid sequence represented by SEQ ID NO. 10, a heterodimer of a protein having an amino acid sequence that is at least 90% identical to the amino acid sequence represented by SEQ ID NO. 8 and a protein having an amino acid sequence that is at least 90% identical to the amino acid sequence represented by SEQ ID NO. 11, or a heterodimer of a protein having an amino acid sequence that is at least 90% identical to the amino acid sequence represented by SEQ ID NO. 9 and a protein having an amino acid sequence that is at least 90% identical to the amino acid sequence represented by SEQ ID NO. 12.

SEQ ID NO. 10 is an amino acid sequence of human HER2 protein consisting of 1,255 amino acids (GenBank Accession Number: NP_001005862.1).

SEQ ID NO. 11 is an amino acid sequence of mouse HER2 protein consisting of 1,256 amino acids (GenBank Accession Number: NP_001003817.1).

SEQ ID NO. 12 is an amino acid sequence of rat HER2 protein consisting of 1,259 amino acids (GenBank Accession Number: NP_058699.2).

In another embodiment, an amphiregulin receptor is a heterodimer of a protein having an amino acid sequence that is at least 95% identical, at least 98% identical, at least 99% identical, or 100% identical to the amino acid sequence represented by SEQ ID NO. 7, 13, 14, 15, 16, or 17, and a protein having an amino acid sequence that is at least 95% identical, at least 98% identical, at least 99% identical, or 100% identical to the amino acid sequence represented by SEQ ID NO. 10, a heterodimer of a protein having an amino acid sequence that is at least 95% identical, at least 98% identical, at least 99% identical, or 100% identical to the amino acid sequence represented by SEQ ID NO. 8, and a protein having an amino acid sequence that is at least 95% identical, at least 98% identical, at least 99% identical, or 100% identical to the amino acid sequence represented by SEQ ID NO. 11, or a heterodimer of a protein having an amino acid sequence that is at least 95% identical, at least 98% identical, at least 99% identical, or 100% identical to the amino acid sequence represented by SEQ ID NO. 9, and a protein having an amino acid sequence that is at least 95% identical, at least 98% identical, at least 99% identical, or 100% identical to the amino acid sequence represented by SEQ ID NO. 12.

In some embodiments, the agent that causes suppression of expression of an amphiregulin receptor, suppression of activation of an amphiregulin receptor, and/or inhibition of binding of an amphiregulin receptor with amphiregulin is selected from the group consisting of a neutralizing antibody against an amphiregulin receptor, an antigen binding fragment of a neutralizing antibody against an amphiregulin receptor, an antisense oligonucleotide against an amphiregulin receptor, a small interfering RNA against an amphiregulin receptor, a ribozyme against an amphiregulin receptor, an aptamer against an amphiregulin receptor, and a low-molecular compound that inhibits proliferation of lymphatic endothelial cells via an amphiregulin receptor. Containing one or more such agents as an active ingredient is effective for the prevention or treatment of cystic lymphangioma.

The neutralizing antibody, the antigen binding fragment of the neutralizing antibody, the antisense oligonucleotide, the small interfering RNA, the ribozyme, and the aptamer are as described in the first aspect of the invention. The neutralizing antibody against an amphiregulin receptor, the antigen binding fragment of the neutralizing antibody, the antisense oligonucleotide, the small interfering RNA, the ribozyme, and the aptamer may be produced by those skilled in the art based on a well-known technique in the art.

The low-molecular compound that inhibits proliferation of lymphatic endothelial cells via an amphiregulin receptor includes low-molecular compounds such as an EGFR tyrosine kinase inhibitor, an HER2 tyrosine kinase inhibitor, and a tyrosine kinase inhibitor of both EGFR and HER2. For example, the low-molecular compound includes Gefitinib, Erlotinib, Afatinib, Osimertinib, Dacomitinib, Lapatinib, Vandetanib, Peritinib, Canertinib, Neratinib, Nazartinib, Lazertinib, Icotinib, Rociletinib, Ormucinib, CK-101(N-(3-(2-((2,3-Difluoro-4-(4-(2-hydroxyethyl)piperazin-1-yl)phenyl)amino)quinazolin-8-yl)phenyl)acrylamide), BMS-690514((3R,4R)-4-amino-1-[[4-(3-methoxyanilino)pyrrolo[2,1-f][1,2,4]triazin-5-yl]methyl]piperidin-3-ol), AEE788(6-{4-[(4-Ethyl-1-piperazinyl)methyl]phenyl}-N-[(1R)-1-phenylethyl]-1H-pyrrolo[2,3-d]pyrimidin-4-amine, CID 10297043, NVP-AEE 788, and [6-[4-[(4-Ethylpiperazin-1-yl)methyl]phenyl]-7H-pyrrolo[2,3-d]pyrimidin-4-yl]-((R)-1-phenylethyl)amine)

The agents of various embodiments according to the second aspect of the invention may control one or more of the following: expression, secretion, localization, and/or activity of a molecule involved in onset or development of cystic lymphangioma upstream or downstream from amphiregulin.

Each of the pharmaceutical compositions of the first and second aspects of the invention is targeted to a mammal, including a human, as a subject, and is administered preferably to a human or mouse, more preferably to a human.

Although the agent that causes suppression of expression of amphiregulin, suppression of secretion of amphiregulin, and/or inhibition of binding of amphiregulin with an amphiregulin receptor, and the agent that causes suppression of expression of an amphiregulin receptor, suppression of activation of an amphiregulin receptor, and/or inhibition of binding of an amphiregulin receptor with amphiregulin, may each be used as a single agent, either of the agents may be used for the prevention or treatment of cystic lymphangioma in combination with interferon α, propranolol, an anticancer drug such as vincristine, bisphosphonate, and octreotide.

The combination with one or more of these drugs not only improves a prevention or treatment effect of cystic lymphangioma by the agent that causes suppression of expression of amphiregulin, suppression of secretion of amphiregulin, and/or inhibition of binding of amphiregulin with an amphiregulin receptor, and the agent that causes suppression of expression of an amphiregulin receptor, suppression of activation of an amphiregulin receptor, and/or inhibition of binding of an amphiregulin receptor with amphiregulin, but also may reduce the dose compared to the case in which a single drug is used. Thus, it is preferable in terms of reduction of side effects.

The pharmaceutical composition of each of the first and second aspects of the invention may be administered to a human in various forms. Such forms may be, for example, an oral preparation, an injectable preparation, an external preparation such as an ointment preparation, and an adhesive patch. These preparations may be produced by methods known to those skilled in the art. In preparation, commonly used pharmaceutically acceptable carriers such as a binder, a disintegrant, a lubricant, a colorant, a flavoring agent, a deodorant, a buffer, a stabilizer, a tonicity agent, a solvent, an excipient, a solubilizer, a dispersant, a suspending agent, a preservative a pain reliever, a pigment, and a perfume may be used.

Among oral preparations, for a solid preparation, the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/or inhibition of binding of an amphiregulin receptor with amphiregulin, an excipient, and, if required, a carrier such as a binder, a disintegrant, a lubricant, a colorant, a flavoring, and a deodorant, is mixed and processed in a standard method to form tablets, coated tablets, granules, powders, capsules, or dry syrup. For a liquid oral preparation, the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/or inhibition of binding of an amphiregulin receptor with amphiregulin, a carrier such as a flavoring agent, a buffer, a stabilizer, and a deodorant, is used and processed in a standard method to form internal fluid, syrup, or an elixir.

For an injectable preparation, the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/or inhibition of binding of an amphiregulin receptor with amphiregulin, is mixed with a pH-adjusting agent, a buffer, a stabilizer, a tonicity agent, or a local anesthetic, and processed in a standard method to form a subcutaneous injectable preparation, an intramuscular injectable preparation, or an intravenous injectable preparation.

Among external preparations, an ointment such as a paste, a cream, and a gel may be prepared by mixing a base including the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/or inhibition of binding of an amphiregulin receptor with amphiregulin with a stabilizer, a wetting agent, or a preservative as required, and treating in a standard method. The base includes, for example, white petrolatum, paraffin, glycerin, cellulose derivatives, polyethylene glycol, silicone, and bentonite. The preservative includes methyl p-hydroxybenzoate, ethyl p-hydroxybenzoate, and propyl p-hydroxybenzoate.

Among external preparations, an adhesive patch may be produced by applying an ointment, a cream, a gel, or a paste to a common support by a standard method. The support is preferably a woven cloth of cotton, staple fibers, or chemical fibers, a non-woven cloth, a film of soft vinyl chloride, polyethylene, or polyurethane, or a foam sheet.

The drug that can be used in combination may be an administration form similar to that of the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/or inhibition of binding of an amphiregulin receptor with amphiregulin. When the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/or inhibition of binding of an amphiregulin receptor with amphiregulin and another drug, is used in combination, they may be a single administration form including them, or two or more administration forms each of which includes either of them. As long as the object of the invention is achieved, separately prepared preparations may be administered to the same subject simultaneously or at different times.

The amount of the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/or inhibition of binding of an amphiregulin receptor with amphiregulin, to be contained in each of the preparations may vary depending on the condition, body weight, age, and sex of a patient to which the agent is administered, or other condition, and may be determined appropriately depending on the dosage form. In general, the dose per day and per 1 kg of body weight of a subject may be as follows: in the case of an oral preparation, from about 1 ng to 1 g; in some embodiments, from 1 μg to 1 g; in some embodiments, from 0.1 mg to 100 mg; in the case of an injectable preparation, from about 1 ng to 500 mg; in some embodiments, from 1 μg to 500 mg; in some embodiments, from 0.1 mg to 50 mg; in the case of a suppository or an external preparation, from about 1 ng to 1 g; in some embodiments, 1 μg to 1 g; in some embodiments, 0.1 mg to 100 mg. The preparation may be administered once in a day or may be divided into twice to four times a day.

The amount of the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/or inhibition of binding of an amphiregulin receptor with amphiregulin, to be contained in the medicament may be determined appropriately depending on the dosage form. Per dosage unit of an adult, the amount may be as follows: in the case of an oral preparation, from about 10 ng to 10 g; in some embodiments, from 10 μg to 1 g; in some embodiments, from 1 mg to 1 g; in the case of an injectable preparation, from about 10 ng to 5 g; in some embodiments, from 10 µg to 5 g; in some embodiments, from 1 mg to 500 mg; in the case of a suppository or an external preparation, from about 10 ng to 10 g; in some embodiments, from 10 µg to 1 g; in some embodiments, from 1 mg to 1 g. The preparation may be administered once in a day or may be divided into twice to four times a day.

In some embodiments, when the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/or inhibition of binding of an amphiregulin receptor with amphiregulin, is an antibody, an antigen binding fragment of an antibody, or an aptamer, the dose of the agent per day and per 1 kg of body weight of a subject is in the range of from 1 ng to 1 g; in some embodiments, 1 µg/day/kg to about 1 g/day/kg; in some embodiments, about 1 µg/day/kg to about 100 mg/day/kg; and in some embodiments, about 1 µg/day/kg to about 10 mg/day/kg.

In some embodiments, when the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/or inhibition of binding of an amphiregulin receptor with amphiregulin, is an antisense oligonucleotide, a small interfering RNA, a ribozyme, or a low-molecular compound, the dose of the agent per day and per 1 kg of body weight of a subject is in the range of from 1 ng to 1 g; in some embodiments, from 1 µg/day/kg to about 1 g/day/kg; in some embodiment, from about 1 µg/day/kg to about 100 mg/day/kg; and in some embodiments, from about 1 µg/day/ kg to about 10 mg/day/kg.

According to a third aspect of the invention, provided is use of an agent of either (a) or (b) for manufacturing a medicament for preventing or treating cystic lymphangioma:

(a) an agent that causes suppression of expression of amphiregulin, suppression of secretion of amphiregulin, and/or inhibition of binding of amphiregulin with an amphiregulin receptor; and (b) an agent that causes suppression of expression of an amphiregulin receptor, suppression of activation of an amphiregulin receptor, and/or inhibition of binding of an amphiregulin receptor with amphiregulin.

The agent that causes suppression of expression of amphiregulin, suppression of secretion of amphiregulin, and/or inhibition of binding of amphiregulin with an amphiregulin receptor, and the agent that causes suppression of expression of an amphiregulin receptor, suppression of activation of an amphiregulin receptor, and/or inhibition of binding of an amphiregulin receptor with amphiregulin, are described with respect to a pharmaceutical composition of the first aspect of the invention and a pharmaceutical composition of the second aspect of the invention, respectively.

According to a fourth aspect of the invention, provided is a medicament for inhibiting proliferation of lymphatic endothelial cells comprising an agent of either (a) or (b) as an active ingredient:

(a) an agent that causes suppression of expression of amphiregulin, suppression of secretion of amphiregulin, and/or inhibition of binding of amphiregulin with an amphiregulin receptor; and (b) an agent that causes suppression of expression of an amphiregulin receptor, suppression of activation of an amphiregulin receptor, and/or inhibition of binding of an amphiregulin receptor with amphiregulin.

The agent that causes suppression of expression of amphiregulin, suppression of secretion of amphiregulin, and/or inhibition of binding of amphiregulin with an amphiregulin receptor, and the agent that causes suppression of expression of an amphiregulin receptor, suppression of activation of an amphiregulin receptor, and/or inhibition of binding of an amphiregulin receptor with amphiregulin, are described with respect to a pharmaceutical composition of the first aspect of the invention and a pharmaceutical composition of the second aspect of the invention, respectively.

Although the agent that causes suppression of expression of amphiregulin, suppression of secretion of amphiregulin, and/or inhibition of binding of amphiregulin with an amphiregulin receptor, and the agent that causes suppression of expression of an amphiregulin receptor, suppression of activation of an amphiregulin receptor, and/or inhibition of binding of an amphiregulin receptor with amphiregulin, may each be used as a single agent, either of the agents may be used for inhibiting proliferation of lymphatic endothelial cells in combination with interferon a, propranolol, an anticancer drug such as vincristine, bisphosphonate, and octreotide.

The medicament according to the fourth aspect of the invention may be administered to a human in various forms. Such forms may be, for example, an oral preparation, an injectable preparation, an external preparation such as an ointment preparation, and an adhesive patch. These preparations may be produced by methods known to those skilled in the art. In preparation, commonly used pharmaceutically acceptable carriers such as a binder, a disintegrant, a lubricant, a colorant, a flavoring agent, a deodorant, a buffer, a stabilizer, a tonicity agent, a solvent, an excipient, a solubilizer, a dispersant, a suspending agent, a preservative, a pain reliever, a pigment, and a perfume may be used.

The lymphatic endothelial cells are those derived from a subject that is a mammal. The subject is preferably a human or mouse, more preferably a human.

The amount of the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/ or inhibition of binding of an amphiregulin receptor with amphiregulin to be contained in a medicament, may be determined depending on the condition of a patient to which the agent is administered or on the dosage form. In general, per dosage unit of an adult, the amount may be as follows: in the case of an oral preparation, from about 10 ng to 10 g; in some embodiments, from 10 µg to 1 g; in some embodiments, from 1 mg to 1 g; in the case of an injectable preparation, from about 10 ng to 5 g; in some embodiments, from 10 µg to 5 g; in some embodiments, from 1 mg to 500 mg; in the case of a suppository or an external preparation, from about 10 ng to 10 g; in some embodiments, from 10 µg to 1 g; in some embodiments, from 1 mg to 1 g. The preparation may be administered once in a day or may be divided into twice to four times a day.

The amount of the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/ or inhibition of binding of an amphiregulin receptor with amphiregulin, to be contained in each of the preparations per day may vary depending on the condition, body weight, age, and sex of a patient to which the agent is administered, or other condition. In general, per dosage unit of an adult, the amount may be as follows: in the case of an oral preparation, from about 10 ng to 10 g; in some embodiments, from 10 μg to 1 g; in some embodiments, from 1 mg to 1 g; in the case of an injectable preparation, from about 10 ng to 5 g; in some embodiments, from 10 μg to 5 g; in some embodiments, from 1 mg to 500 mg; in the case of a suppository or an external preparation, from about 10 ng to 10 g; in some embodiments, from 10 μg to 1 g; in some embodiments, from 1 mg to 1 g. The preparation may be administered once in a day or may be divided into twice to four times a day.

According to a fifth aspect of the invention, provided is a kit preventing or treating cystic lymphangioma comprising an agent of either (a) or (b):

> (a) an agent that causes suppression of expression of amphiregulin, suppression of secretion of amphiregulin, and/or inhibition of binding of amphiregulin with an amphiregulin receptor; and
>
> (b) an agent that causes suppression of expression of an amphiregulin receptor, suppression of activation of an amphiregulin receptor, and/or inhibition of binding of an amphiregulin receptor with amphiregulin.

The agent that causes suppression of expression of amphiregulin, suppression of secretion of amphiregulin, and/or inhibition of binding of amphiregulin with an amphiregulin receptor, and the agent that causes suppression of expression of an amphiregulin receptor, suppression of activation of an amphiregulin receptor, and/or inhibition of binding of an amphiregulin receptor with amphiregulin, are described with respect to a pharmaceutical composition of the first aspect of the invention and a pharmaceutical composition of the second aspect of the invention, respectively.

The kit may further comprise instructions for conducting a test. The kit may further comprise a container for containing the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/or inhibition of binding of an amphiregulin receptor with amphiregulin. The kit may further comprise a solvent for dissolving or suspending the agent that causes suppression of expression of amphiregulin, suppression of secretion of amphiregulin, and/or inhibition of binding of amphiregulin with an amphiregulin receptor, or the agent that causes suppression of expression of an amphiregulin receptor, suppression of activation of an amphiregulin receptor, and/or inhibition of binding of an amphiregulin receptor with amphiregulin. The kit may further comprise a preservative or a pH control agent.

According to a sixth aspect of the invention, a method for testing cystic lymphangioma comprising measuring amphiregulin or an amphiregulin receptor in a sample collected from a subject is provided.

The subject is a mammal, including, preferably, a human or mouse, more preferably a human.

The sample collected from a subject may be a tissue or cells. For example, the sample includes a lymphatic tissue, lymphatic endothelial cells, and fibroblast cells around one or more lymph vessels.

As used herein, the "test" of cystic lymphangioma includes determination of cystic lymphangioma, determination of cystic lymphangioma (a responder) for which a therapeutic agent is effective (companion diagnosis), determination of a prevention effect of cystic lymphangioma, determination of a treatment effect of cystic lymphangioma, a method for testing for aiding diagnosis (particularly, early diagnosis) of cystic lymphangioma, and a method for testing for aiding treatment (particularly, early treatment) of cystic lymphangioma. The "determination" of cystic lymphangioma not only includes determination of presence or absence of cystic lymphangioma but also preventive determination of the possibility of incidence of cystic lymphangioma, prediction of prognosis of cystic lymphangioma after the treatment, and determination of the treatment effect of a therapeutic agent for cystic lymphangioma.

Amphiregulin or an amphiregulin receptor is found in a sample collected from a subject. The measurement values of these proteins correlate with cystic lymphangioma. Specifically, the expression of amphiregulin and an amphiregulin receptor in a sample is significantly higher in a subject suffering from cystic lymphangioma than in a normal subject. In addition, the expression of amphiregulin and an amphiregulin receptor in a sample is significantly higher in a PDGFRβ-knockout mouse than in a normal mouse.

Thus, when the level of amphiregulin in a sample collected from a subject is the same as or lower than the level of amphiregulin in a sample collected from a normal subject, it means that the possibility of incidence of cystic lymphangioma is low in the subject and can be so determined. Hereinafter, "level" refers to concentration, amount, or signal strength. When the level of amphiregulin in a sample collected from a subject is the same as or higher than the average value or the middle value of the level of amphiregulin in samples collected from patients with cystic lymphangioma or a cutoff value that distinguishes between the level of amphiregulin in samples collected from patients with cystic lymphangioma and the level of amphiregulin in samples collected from normal subjects, it means that the possibility of incidence of cystic lymphangioma is high in the subject and can be so determined.

Similarly, when the level of an amphiregulin receptor in a sample collected from a subject is the same as or lower than the level of an amphiregulin receptor in a sample collected from a normal subject, it means that the possibility of incidence of cystic lymphangioma is low in the subject and can be so determined. When the level of an amphiregulin receptor in a sample collected from a subject is the same as or higher than the average value or the middle value of the level of an amphiregulin receptor in samples collected from patients with cystic lymphangioma or a cutoff value that distinguishes between the level of an amphiregulin receptor in samples collected from patients with cystic lymphangioma and the level of an amphiregulin receptor in samples collected from normal subjects, it means that the possibility of incidence of cystic lymphangioma is high in the subject and can be so determined.

Further, a method for testing cystic lymphangioma comprising collecting samples over time can be used in evaluating a treatment effect of measures for treating the disease when such measures were taken for a patient who is a subject between the previous sampling and the sampling this time.

The measures include administration of an agent that causes suppression of expression of amphiregulin, suppression of secretion of amphiregulin, and/or inhibition of binding of amphiregulin with an amphiregulin receptor, or an agent that causes suppression of expression of an amphiregulin receptor, suppression of activation of an amphiregulin receptor, and/or inhibition of binding of an amphiregulin receptor with amphiregulin to a patient (or a subject), administration of a pharmaceutical composition of the first aspect to a patient (or a subject), administration of a pharmaceutical composition of the second aspect to a patient (or a subject) or administration of a medicament of the fourth aspect to a patient (or a subject), administration of a known drug for cystic lymphangioma, a diet therapy, and an exercise therapy.

When the decrease in the level of amphiregulin or an amphiregulin receptor in a sample is observed when the sample before the measures and the sample after the measures are compared, it indicates that the measures are effective and can be so determined. On the other hand, when the change in the level of amphiregulin or an amphiregulin receptor in a sample is not observed or the level is increased when the sample before the measures and the sample after the measures are compared, it indicates that the measures are not effective and can be so determined.

Accordingly, the test method according to the sixth aspect of the invention may be used for screening a substance, particularly a drug, that is effective for the treatment of cystic lymphangioma. For example, a method for screening a substance that is effective for the treatment of cystic lymphangioma according to one embodiment of the invention comprises preparing lymphatic endothelial cells or fibroblast cells around one or more lymph vessels of an animal (preferably a human or mouse, more preferably a human), contacting a test substance with the cells, and detecting the change in the level of amphiregulin or an amphiregulin receptor in the cells after contacting with the test substance. The details of amphiregulin and an amphiregulin receptor are described with respect to the second aspect. The level of amphiregulin and level of an amphiregulin receptor may be the level of the protein or the level of mRNA. When the level of amphiregulin in the cells is lower after contact compared with the level before contact, it indicates that the test substance is a candidate that is effective for the treatment of cystic lymphangioma and the test substance can be selected. Alternatively, when the level of amphiregulin is the same or higher after contact compared with the level before contact, it indicates that the test substance is not a candidate that is effective for the treatment of cystic lymphangioma and can be so determined.

According to a seventh aspect of the invention, provided is a test kit for cystic lymphangioma comprising either (a) or (b):

(a) a substance that binds amphiregulin selected from the group consisting of a neutralizing antibody against amphiregulin, an antigen binding fragment of a neutralizing antibody against amphiregulin and an aptamer against amphiregulin, a substance that binds DNA encoding amphiregulin, a substance that binds mRNA transcribed based on DNA encoding amphiregulin as a template, and cDNA reverse-transcribed based on amphiregulin mRNA as a template; and (b) a substance that binds an amphiregulin receptor selected from the group consisting of a neutralizing antibody against an amphiregulin receptor, an antigen binding fragment of a neutralizing antibody against an amphiregulin receptor and an aptamer against an amphiregulin receptor, a substance that binds DNA encoding an amphiregulin receptor, a substance that binds mRNA transcribed based on DNA encoding an amphiregulin receptor as a template, and cDNA reverse-transcribed based on amphiregulin receptor mRNA as a template.

The substance that binds DNA encoding amphiregulin of (a) includes, for example, a polynucleotide (DNA or RNA) that selectively hybridizes with DNA encoding amphiregulin. Such a polynucleotide may be easily produced or obtained by those skilled in the art by producing a polynucleotide (the length being about 15 to 25 nucleotides, for example) that has a sequence complementary to at least a portion of the DNA encoding amphiregulin. The substance that binds mRNA transcribed based on DNA encoding amphiregulin as a template includes, for example, a polynucleotide (DNA or RNA) that selectively hybridizes with mRNA transcribed based on DNA encoding amphiregulin. Such a polynucleotide may be easily produced or obtained by those skilled in the art by producing a polynucleotide (the length being about 15 to 25 nucleotides, for example) that has a sequence complementary to at least a portion of the mRNA transcribed based on DNA encoding amphiregulin.

The substance that binds DNA encoding an amphiregulin receptor of (b) includes, for example, a polypeptide (DNA or RNA) that selectively hybridizes with DNA encoding an amphiregulin receptor. Such a polynucleotide may be easily produced or obtained by those skilled in the art by producing a polynucleotide (the length being about 15 to 25 nucleotides, for example) that has a sequence complementary to at least a portion of the DNA encoding an amphiregulin receptor. The substance that binds mRNA transcribed based on DNA encoding an amphiregulin receptor as a template includes, for example, a polynucleotide (DNA or RNA) that selectively hybridizes with mRNA transcribed based on DNA encoding an amphiregulin receptor. Such a polynucleotide may be easily produced or obtained by those skilled in the art by producing a polynucleotide (the length being about 15 to 25 nucleotides, for example) that has a sequence complementary to at least a portion of the mRNA transcribed based on DNA encoding an amphiregulin receptor.

The kit may further comprise instructions for conducting a test. The kit may further comprise a container for containing either substance (a) or (b). The kit may further comprise a solvent for dissolving or suspending either substance (a) or (b). The kit may further comprise a preservative or a pH control agent.

The test using the test kit is conducted using a sample collected from a subject. The subject, the sample collected from the subject, and the test method are as described with respect to the test method according to the sixth aspect of the invention.

According to an eighth aspect of the invention, provided is a test kit for cystic lymphangioma comprising either substance (a) or (b):

(a) a pair of oligonucleotide primers for amplifying at least a portion of the nucleic acid sequence of a DNA encoding amphiregulin, an mRNA transcribed based on the DNA as a template, or a cDNA transcribed based on the mRNA; and (b) a pair of oligonucleotide primers for amplifying at least a portion of the nucleic acid sequence of a DNA encoding an amphiregulin receptor, an mRNA transcribed based on the DNA as a template, or a cDNA transcribed based on the mRNA.

The pair of primers of (a) are designed to have sequences that are complementary with a target nucleic acid sequence of a DNA encoding amphiregulin, an mRNA transcribed based on the DNA as a template, or a cDNA transcribed based on the mRNA, and to couple with the target nucleic acid sequence at both ends of the target nucleic acid sequence. The pair of primers of (b) are designed to have sequences that are complementary with a target nucleic acid sequence of a DNA encoding an amphiregulin receptor, an mRNA transcribed based on the DNA as a template, or a cDNA transcribed based on the mRNA, and to couple with the target nucleic acid sequence at both ends of the target nucleic acid sequence. The primers preferably amplify the sequence having 10 to 200 bases. In one embodiment, the lower limit of the length of the primers is at least 12 bases, at least 15 bases, or at least 18 bases. The amplification reaction using a pair of specific primers (a forward primer and a reverse primer) is known as PCR, and design of the pair of such primers for nucleic acid amplification is well known to those skilled in the art.

The test using the test kit is conducted using a sample collected from a subject. By using the test kit for cystic lymphangioma, presence and/or amount of amphiregulin or an amphiregulin receptor in the sample may be detected. The subject, the sample collected from the subject, and the test method are as described with respect to the test method according to the sixth aspect of the invention.

The kit may further comprise instructions for conducting a test. The kit may further comprise a container for containing the first and second primers. The kit may further comprise a solvent for dissolving or suspending the first and the second primers. The kit may further comprise a preservative or a pH control agent.

The test using the test kit is conducted using a sample collected from a subject. The subject, the sample collected from the subject, and the test method are as described with respect to the test method according to the sixth aspect of the invention.

According to a ninth aspect of the invention, provided is a test agent for cystic lymphangioma comprising either substance (a) or (b):

(a) a substance that binds amphiregulin selected from the group consisting of a neutralizing antibody against amphiregulin, an antigen binding fragment of a neutralizing antibody against amphiregulin and an aptamer against amphiregulin, a substance that binds DNA encoding amphiregulin, a substance that binds mRNA transcribed based on DNA encoding amphiregulin as a template, and cDNA reverse-transcribed based on amphiregulin mRNA as a template; and (b) a substance that binds an amphiregulin receptor selected from the group consisting of a neutralizing antibody against an amphiregulin receptor, an antigen binding fragment of a neutralizing antibody against an amphiregulin receptor and an aptamer against an amphiregulin receptor, a substance that binds DNA encoding an amphiregulin receptor, a substance that binds mRNA transcribed based on DNA encoding an amphiregulin receptor as a template, and cDNA reverse-transcribed based on amphiregulin receptor mRNA as a template.

The details of substance (a) and (b) are as described with respect to the test kit for cystic lymphangioma according to the seventh aspect.

The test is conducted using a sample collected from a subject. The subject, the sample collected from the subject, and the test method are as described with respect to the test method according to the sixth aspect of the invention.

The disclosures of all the patent applications and literature are incorporated herein by reference in their entirety.

The invention will be explained in more detail by referring to the following examples, but the invention is not limited to these examples.

EXAMPLES

Example 1: Expression of Amphiregulin in Fibroblast Cells in Lymphatic Vessels in PDGFRβ Knockout Mice 1. Preparation of PDGFRβ Knockout Mice PDGFRβ knockout mice were produced based on Stem Cells, 2016 March; 34(3): 685-98. doi: 10.1002/stem.2212; EBioMedicine, 2018 May; 31: 190-201. doi: 10.1016/j.ebiom.2018.04.021.

2 Immunostaining

The tissues of the PDGFRβ knockout mice, or the cells that were collected from the DGFRβ knockout mice and cultured, were fixed with paraformaldehyde (PFA). Next, the sample of the fixed tissues or cells was washed with a buffer and antigen-retrieved by heating in a microwave oven for 5 minutes using a commercial retrieval solution. Next, each sample was washed with a buffer and the tissues or the cells were subjected to a commercial blocking solution (room temperature, one hour). Next, each sample was washed with a buffer and the tissues or the cells were subjected to an anti-amphiregulin antibody (Santa Cruz Biotechnology) and an anti-LYVE1 antibody (Abcam or Thermo Fisher Scientific), both of which are primary antibodies, at optimum concentration (4° C., overnight). Next, each sample was washed with a buffer and the tissues or the cells were subjected to an antibody against the animal species that produced the anti-amphiregulin antibody (a secondary antibody having a fluorescent dye for visualization) and an antibody against the animal species that produced the anti-LYVE1 antibody (a secondary antibody having a fluorescent dye for visualization) at optimum concentration (4° C., overnight). To dye the nucleus, Hoechst was mixed in a reaction solution of the secondary antibodies at optimum concentration. Then, each sample was washed with a buffer and mounted with a commercial mounting medium. The obtained sample was observed and photographed with a fluorescence microscope.

3. Western Blot Analysis

The tissues of PDGFRβ knockout mice and control mice, and the cells that were collected from PDGFRβ knockout mice and control mice and cultured, were lysed in a commercial lysis buffer (formation of lysates). A sample buffer containing a reduction agent was added to each lysate in an optimum amount and heated at 95° C. for 5 to 10 minutes (formation of samples for western blotting). Each of the samples for western blotting was subjected to polyacrylamide electrophoresis in an optimum amount (normally, 5 to 30 μL) to separate proteins according to their molecular weight. The separated proteins in the gel were transferred to a membrane using a blotting device, and the membrane was blocked with commercial fat-free milk and washed with a buffer. Then, the membrane was subjected to an anti-amphiregulin antibody (Santa Cruz Biotechnology, a primary antibody) (4° C., overnight) and washed with a buffer. Next, the amphiregulin protein derived from the tissues or the cells on the membrane was subjected to an antibody against the animal species that produced the anti-amphiregulin antibody (Nichirei Bioscience Inc., a secondary antibody having HRP) at optimum concentration and washed with a buffer. Using a commercial chemiluminescent reagent, a band of amphiregulin was made luminous. The band of amphiregulin was photographed with a commercial imaging device.

4. Statistical Analysis

The density of the band of amphiregulin obtained from the result of western blot analysis was measured with ImageJ imaging software. The t-test was conducted with commercial software for statistical analysis and tested for a significant difference between the PDGFRβ knockout group and the control group.

5. Results

As shown in FIG. 2A, according to immunostaining of fibroblasts around lymphangioma of PDGFRβ knockout mice, increase in the expression of amphiregulin was observed. As shown in FIG. 2B, when the expression of amphiregulin was compared between the control group of normal mice and the group of PDGFRβ knockout mice, a significant difference was observed in western blot analysis of the tissues.

Example 2: Expression of Amphiregulin in Human Cystic Lymphangioma

1. Preparation of Samples

Paraffin sections were prepared from paraffin blocks of human tissues (three specimens from patients with cystic lymphangioma and three specimens from subjects with other diseases of a control group). Prior informed consent was obtained from each subject.

2 Immunostaining

Paraffin sections were prepared from paraffin blocks of human tissues (three specimens from patients with cystic lymphangioma and three specimens from subjects with other diseases of a control group). Deparaffinization was conducted. The sample of the tissue sections was antigen-retrieved by heating in a microwave oven for 5 minutes using a commercial retrieval solution. Next, each sample was washed with a buffer and the tissues or the cells were subjected to a commercial blocking solution (room temperature, one hour). Next, each sample was washed with a buffer and the tissues or the cells were subjected to an anti-amphiregulin antibody (Santa Cruz Biotechnology) and an anti-podoplanin antibody (Nichirei Bioscience Inc.), both of which are primary antibodies, at optimum concentration (4° C., overnight). Next, each sample was washed with a buffer and the tissues or the cells were subjected to an antibody against the animal species that produced the anti-amphiregulin antibody (a secondary antibody having a fluorescent dye for visualization) and an antibody against the animal species that produced the anti-podoplanin antibody (a secondary antibody having a fluorescent dye for visualization) at optimum concentration (4° C., overnight). To dye the nucleus, Hoechst was mixed in a reaction solution of the secondary antibodies at optimum concentration. Then, each sample was washed with a buffer and mounted with a commercial mounting medium. The obtained sample was observed and photographed with a fluorescence microscope.

3. Pixel Analysis

The portions that were amphiregulin-positive and podoplanin-negative (an interstitium where the cells are present) were cut randomly in the range of 50 μm×50 μm. The number of amphiregulin-positive pixels was measured with ImageJ imaging software. 16 areas were measured for each of three specimens from patients with cystic lymphangioma and three specimens from subjects with other diseases of a control group.

4. Statistical Processing

The t-test was conducted with commercial software for statistical analysis and tested for a significant difference between the group of patients with cystic lymphangioma and the control group.

5. Results

As shown in FIG. 3A, when the expression of amphiregulin was examined using samples of human cystic lymphangioma, significantly higher expression of amphiregulin was confirmed in fibroblasts around lymphangioma (lower side of FIG. 3A) compared with the control group (upper side of FIG. 3A).

The endothelial cells in the cystic lymph vessels also expressed amphiregulin (FIG. 3A) and the expression of amphiregulin in lymphatic endothelial cells significantly increased in co-culture of the fibroblasts and lymphatic endothelial cells (data not shown). Thus, it was revealed that the expression of amphiregulin in fibroblast cells induced expression of amphiregulin in lymphatic endothelial cells as a trigger, and amphiregulin of these two sources induced abnormal proliferation of lymphatic endothelial cells via amphiregulin receptors expressed in lymphatic endothelial cells.

Figure 3B:
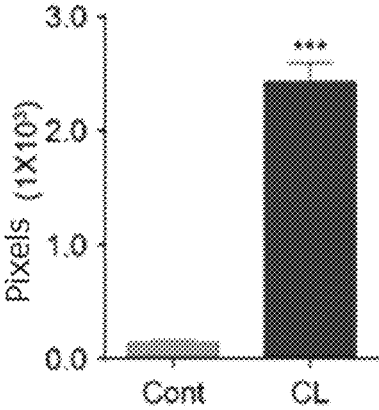
FIG. 3B is pixel analysis of expression of amphiregulin in fibroblasts. Cont: control group; CL: a group of patients with human cystic lymphangioma. *** is <0.001.

As shown in FIG. 3B, when the expression of amphiregulin between the control group, i.e., fibroblasts of a normal human, and fibroblasts of patients with cystic lymphangioma were compared, a significant difference was observed in pixel analysis of the tissues.

Example 3: Expression of an Amphiregulin Receptor in Human Cystic Lymphangioma

1. Preparation of the Sample

Paraffin sections were prepared from paraffin blocks of human tissues (three specimens from patients with cystic lymphangioma and three specimens from subjects with other diseases of a control group). Prior informed consent was obtained from each subject.

2 Immunostaining

Paraffin sections were prepared from paraffin blocks of human tissues (three specimens from patients with cystic lymphangioma and three specimens from subjects with other diseases of a control group). Deparaffinization was conducted. The sample of the tissue sections was antigen-retrieved by heating in a microwave oven for 5 minutes using a commercial retrieval solution. Next, each sample was washed with a buffer and the tissues or the cells were subjected to a commercial blocking solution (room temperature, one hour).

Next, each sample was washed with a buffer and the tissues or the cells were subjected to an anti-phosphorylated EGFR antibody (Cell Signaling Technology) and an anti-podoplanin antibody (Nichirei Bioscience Inc.), both of which are primary antibodies, at optimum concentration (4° C., overnight). Next, each sample was washed with a buffer and the tissues or the cells were subjected to an antibody against the animal species that produced the anti-phosphorylated EGFR antibody (Thermo Fisher Scientific) (a secondary antibody having a fluorescent dye for visualization) and an antibody against the animal species that produced the anti-podoplanin antibody (Thermo Fisher Scientific) (a secondary antibody having a fluorescent dye for visualization) at optimum concentration (4° C., overnight). To dye the nucleus, Hoechst was mixed in a reaction solution of the secondary antibodies at optimum concentration. Then, each sample was washed with a buffer and mounted with a commercial mounting medium. The obtained sample was observed and photographed with a fluorescence microscope.

3. Results

Figure 4:
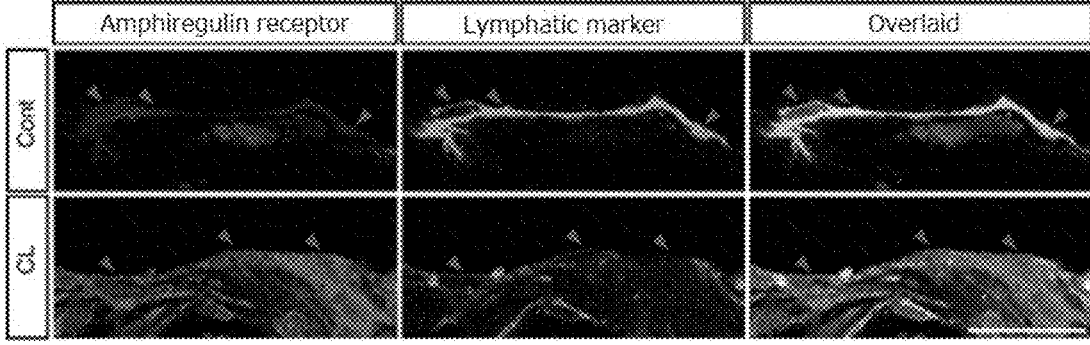
FIG. 4 is immunohistological staining of cystic lymphatic endothelial cells in a tissue derived from a patient with human cystic lymphangioma. Left: phosphorylated amphiregulin receptor (pEGFR); middle: lymphatic marker (podoplanin); right: an overlaid image of phosphorylated amphiregulin receptor (pEGFR), lymphatic marker (podoplanin), and nucleus. Cont: control group; CL: a group of patients with human cystic lymphangioma. The scale bar is 20 μm.

As shown FIG. 4, a signal of an amphiregulin receptor was activated in cystic lymphatic endothelial cells in tissues derived from patients with human cystic lymphangioma (image of phosphorylated EGFR extremely positive; lower side of FIG. 4), which supports abnormal proliferation of lymphatic endothelial cells. In the control group (upper side of FIG. 4), the signal of an amphiregulin receptor was at an extremely lower level and phosphorylated EGFR positive level was lower than that of the control group.

Example 4: Therapy Experiment in Cystic Lymphangioma of PDGFRβ Knockout Mice 1. Preparation of PDGFRβ Knockout Mice PDGFRβ knockout mice were produced based on Stem Cells, 2016 March; 34(3): 685-98. doi: 10.1002/stem.2212; EBioMedicine, 2018 May; 31: 190-201. doi: 10.1016/j.ebiom.2018.04.021.

2. Administration of a Therapeutic Agent

To PDGFRβ knockout mice, a neutralizing antibody against amphiregulin (AF989, R&D Systems Inc.) and Erlotinib having EGFR inhibitory activity (Selleck Biotech) were administered for the purpose of treating cystic lymphangioma. The neutralizing antibody against amphiregulin was dissolved in PBS at 25 µg/mL and administered intraperitoneally at 5 µg/body three times a week. Erlotinib was dissolved in DMSO at 50 mg/mL and administered intraperitoneally at 50 mg/kg three times a week. A group of PDGFRβ knockout mice without treatment and a control group of mice in which PDGFRβ was not knocked out were also prepared.

3 Immunostaining

The tissues of PDGFRβ knockout mice were fixed with paraformaldehyde (PFA). Paraffin sections were prepared using fixed samples. The tissue sections were washed with a buffer and antigen-retrieved by heating in a microwave oven for 5 minutes using a commercial retrieval solution. Next, each sample was washed with a buffer solution and the tissues or the cells were subjected to a commercial blocking solution (room temperature, one hour).

Next, each sample was washed with a buffer and subjected to an anti-LYVE1 antibody (Abcam, a primary antibody) at optimum concentration (4° C., overnight). Next, each sample was washed with a buffer and subjected to an antibody against the animal species that produced the anti-LYVE1 antibody (Nichirei Bioscience Inc., a secondary antibody having HRP for visualization) at optimum concentration (4° C., overnight). Next, each sample was washed with a buffer and subjected to DAB to visualize lymphatic endothelial cells. To dye the nucleus, hematoxylin action was performed at optimum concentration. Then, each sample was washed with a buffer and mounted with a commercial mounting medium. The obtained sample was observed and photographed with a fluorescence microscope.

4. Statistical Processing

The diameter of each lymph vessel was measured with ImageJ imaging software based on the photographed images. A test was conducted with commercial software for statistical analysis and tested for a significant difference between the group of PDGFRβ knockout mice with treatment, the group of PDGFRβ knockout mice without treatment, and the control group of mice in which PDGFRβ was not knocked out.

5. Results

Figure 5A:
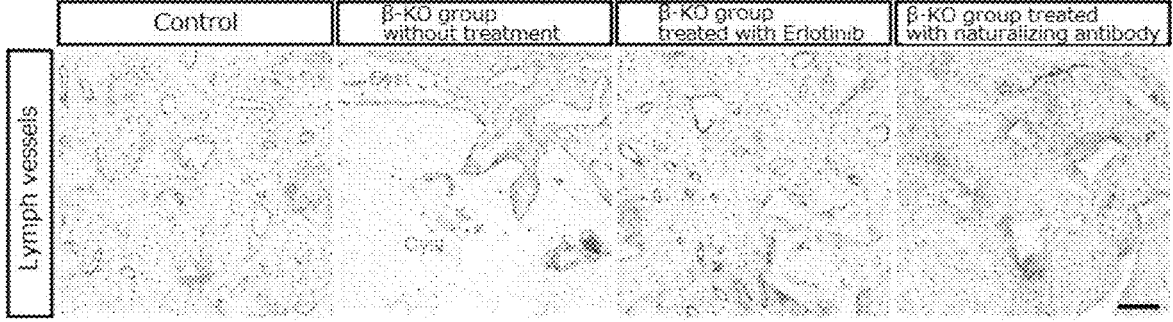
FIG. 5A is morphology of LYVE1-positive lymph vessels. Left: a control group in which PDGFRβ is not knocked out; left middle: a group of PDGFRβ knockout mice without treatment; right middle: PDGFRβ knockout mice treated with Erlotinib; right: PDGFR β knockout mice treated with an amphiregulin-neutralizing antibody. The scale bar is 100 μm.
Figure 5B:
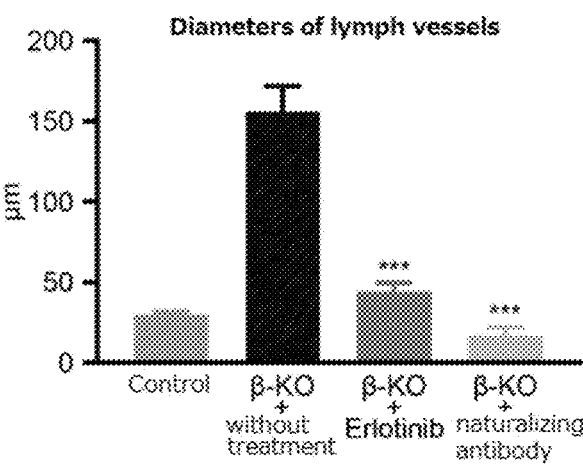
FIG. 5B is results of statistical analysis of diameters of lymph vessels. *** is <0.001.

As shown in FIGS. 5A and 5B, the diameter of dilated lymph vessels of PDGFRβ knockout mice was significantly reduced by the administration of Erlotinib or the neutralizing antibody of amphiregulin compared with the group of PDGFRβ knockout mice without treatment. It was indicated that the diameter of the vessels of PDGFRβ knockout mice with treatment was recovered to the same extent as the control group of mice in which PDGFRβ was not knocked out.

INDUSTRIAL APPLICABILITY

The prevent invention enables development or provision of a molecular-targeted therapeutic drug against human cystic lymphangioma for which there exists no basic therapeutic agent. It is expected that the agent that causes suppression of expression of amphiregulin, suppression of secretion of amphiregulin, and/or inhibition of binding of amphiregulin with an amphiregulin receptor, and the agent that causes suppression of expression of an amphiregulin receptor, suppression of activation of an amphiregulin receptor, and/or inhibition of binding of an amphiregulin receptor with amphiregulin, will each become an effective medicament.

The invention claimed is:

1. A method for treating cystic lymphangioma comprising administering to a subject in need thereof an effective amount of an agent as an active ingredient (i) that causes suppression of expression of amphiregulin, suppression of secretion of amphiregulin, and/or inhibition of binding of amphiregulin with an amphiregulin receptor, or (ii) that causes suppression of expression of an amphiregulin receptor, suppression of activation of an amphiregulin receptor, and/or inhibition of binding of an amphiregulin receptor with amphiregulin.

2. The method according to claim 1, wherein the agent is selected from the group consisting of a neutralizing antibody against amphiregulin, an antigen binding fragment of a neutralizing antibody against amphiregulin.

3. The method according to claim 1, wherein the agent is selected from the group consisting of a neutralizing antibody against an amphiregulin receptor, an antigen binding fragment of a neutralizing antibody against an amphiregulin receptor, and an EGFR tyrosine kinase inhibitor.

4. A method for testing cystic lymphangioma comprising collecting a sample from a subject, measuring amphiregulin or an amphiregulin receptor in the sample by using a test agent, and treating the subject, wherein the treatment is selected from the group consisting of administration of a medicinal agent, exercise therapy, and dietary therapy, and wherein the test agent comprises either substance of (a) or (b):

(a) a substance that binds amphiregulin selected from the group consisting of a neutralizing antibody against amphiregulin, an antigen binding fragment of a neutralizing antibody against amphiregulin and an aptamer against amphiregulin, a substance that binds DNA encoding amphiregulin, a substance that binds mRNA transcribed based on DNA encoding amphiregulin as a template, and cDNA reverse-transcribed based on amphiregulin mRNA as a template; and (b) a substance that binds an amphiregulin receptor selected from the group consisting of a neutralizing antibody against an amphiregulin receptor, an antigen binding fragment of a neutralizing antibody against an amphiregulin receptor and an aptamer against an amphiregulin receptor, a substance that binds DNA encoding an amphiregulin receptor, a substance that binds mRNA transcribed based on DNA encoding an amphiregulin receptor as a template, and cDNA reverse-transcribed based on amphiregulin receptor mRNA as a template.

5. A method for determining cystic lymphangioma comprising collecting a sample from a subject, measuring a level of amphiregulin or an amphiregulin receptor in the sample by using a test agent, determining that when the level of amphiregulin or an amphiregulin receptor in a sample collected from a subject is the same as or lower than the level of amphiregulin or an amphiregulin receptor in a sample collected from a normal subject, it means that the possibility of incidence of cystic lymphangioma is low in the subject, or that the level of amphiregulin in a sample collected from a subject is the same as or higher than the average value or the middle value of the level of amphiregulin in samples collected from patients with cystic lymphangioma or a cutoff value that distinguishes between the level of amphiregulin in samples collected from patients with cystic lymphangioma and the level of amphiregulin in samples collected from normal subjects, it means that the possibility of incidence of cystic lymphangioma is high in the subject, and treating the subject wherein the treatment is selected from the group consisting of administration of a medicinal agent, exercise therapy, and dietary therapy, and wherein the test agent comprises either substance of (a) or (b):

(a) a substance that binds amphiregulin selected from the group consisting of a neutralizing antibody against amphiregulin, an antigen binding fragment of a neutralizing antibody against amphiregulin and an aptamer against amphiregulin, a substance that binds DNA encoding amphiregulin, a substance that binds mRNA transcribed based on DNA encoding amphiregulin as a template, and cDNA reverse-transcribed based on amphiregulin mRNA as a template; and (b) a substance that binds an amphiregulin receptor selected from the group consisting of a neutralizing antibody against an amphiregulin receptor, an antigen binding fragment of a neutralizing antibody against an amphiregulin receptor and an aptamer against an amphiregulin receptor, a substance that binds DNA encoding an amphiregulin receptor, a substance that binds mRNA transcribed based on DNA encoding an amphiregulin receptor as a template, and cDNA reverse-transcribed based on amphiregulin receptor mRNA as a template.

* * * * *

SEQUENCE LISTING

```
<160> NUMBER OF SEQ ID NOS: 17

<210> SEQ ID NO 1
<211> LENGTH: 252
<212> TYPE: PRT
<213> ORGANISM: Homo sapiens

<400> SEQUENCE: 1

Met Arg Ala Pro Leu Leu Pro Pro Ala Pro Val Val Leu Ser Leu Leu
1               5                   10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

Phe Glu Val Thr Ser Arg Ser Glu Met Ser Ser Gly Ser Glu Ile Ser
    50                  55                  60

Pro Val Ser Glu Met Pro Ser Ser Ser Glu Pro Ser Ser Gly Ala Asp
65                  70                  75                  80

Tyr Asp Tyr Ser Glu Glu Tyr Asp Asn Glu Pro Gln Ile Pro Gly Tyr
```

```
                    85                 90                 95
Ile Val Asp Asp Ser Val Arg Val Glu Gln Val Val Lys Pro Pro Gln
                100                105                110

Asn Lys Thr Glu Ser Glu Asn Thr Ser Asp Lys Pro Lys Arg Lys Lys
            115                120                125

Lys Gly Gly Lys Asn Gly Lys Asn Arg Arg Asn Arg Lys Lys Lys Asn
        130                135                140

Pro Cys Asn Ala Glu Phe Gln Asn Phe Cys Ile His Gly Glu Cys Lys
145                150                155                160

Tyr Ile Glu His Leu Glu Ala Val Thr Cys Lys Cys Gln Gln Glu Tyr
                165                170                175

Phe Gly Glu Arg Cys Gly Glu Lys Ser Met Lys Thr His Ser Met Ile
                180                185                190

Asp Ser Ser Leu Ser Lys Ile Ala Leu Ala Ala Ile Ala Ala Phe Met
            195                200                205

Ser Ala Val Ile Leu Thr Ala Val Ala Val Ile Thr Val Gln Leu Arg
        210                215                220

Arg Gln Tyr Val Arg Lys Tyr Glu Gly Glu Ala Glu Glu Arg Lys Lys
225                230                235                240

Leu Arg Gln Glu Asn Gly Asn Val His Ala Ile Ala
                245                250

<210> SEQ ID NO 2
<211> LENGTH: 87
<212> TYPE: PRT
<213> ORGANISM: Homo sapiens

<400> SEQUENCE: 2

Ser Val Arg Val Glu Gln Val Val Lys Pro Pro Gln Asn Lys Thr Glu
1               5                  10                 15

Ser Glu Asn Thr Ser Asp Lys Pro Lys Arg Lys Lys Lys Gly Gly Lys
            20                 25                 30

Asn Gly Lys Asn Arg Arg Asn Arg Lys Lys Lys Asn Pro Cys Asn Ala
        35                 40                 45

Glu Phe Gln Asn Phe Cys Ile His Gly Glu Cys Lys Tyr Ile Glu His
    50                 55                 60

Leu Glu Ala Val Thr Cys Lys Cys Gln Gln Glu Tyr Phe Gly Glu Arg
65                 70                 75                 80

Cys Gly Glu Lys Ser Met Lys
                85

<210> SEQ ID NO 3
<211> LENGTH: 248
<212> TYPE: PRT
<213> ORGANISM: Mus musculus

<400> SEQUENCE: 3

Met Arg Thr Pro Leu Leu Pro Leu Ala Arg Ser Val Leu Leu Leu Leu
1               5                  10                 15

Val Leu Gly Ser Gly His Tyr Ala Ala Ala Leu Glu Leu Asn Asp Pro
            20                 25                 30

Ser Ser Gly Lys Gly Glu Ser Leu Ser Gly Asp His Ser Ala Gly Gly
        35                 40                 45

Leu Glu Leu Ser Val Gly Arg Glu Val Ser Thr Ile Ser Glu Met Pro
    50                 55                 60

Ser Gly Ser Glu Leu Ser Thr Gly Asp Tyr Asp Tyr Ser Glu Glu Tyr
```

```
65                    70                    75                    80

Asp Asn Glu Pro Gln Ile Ser Gly Tyr Ile Ile Asp Asp Ser Val Arg
                    85                    90                    95

Val Glu Gln Val Ile Lys Pro Lys Lys Asn Lys Thr Glu Gly Glu Lys
                    100                   105                   110

Ser Thr Glu Lys Pro Lys Arg Lys Lys Lys Gly Gly Lys Asn Gly Lys
                    115                   120                   125

Gly Arg Arg Asn Lys Lys Lys Asn Pro Cys Thr Ala Lys Phe Gln
                    130                   135                   140

Asn Phe Cys Ile His Gly Glu Cys Arg Tyr Ile Glu Asn Leu Glu Val
145                   150                   155                   160

Val Thr Cys Asn Cys His Gln Asp Tyr Phe Gly Glu Arg Cys Gly Glu
                    165                   170                   175

Lys Ser Met Lys Thr His Ser Glu Asp Asp Lys Asp Leu Ser Lys Ile
                    180                   185                   190

Ala Val Val Ala Val Thr Ile Phe Val Ser Ala Ile Ile Leu Ala Ala
                    195                   200                   205

Ile Gly Ile Gly Ile Val Ile Thr Val His Leu Trp Lys Arg Tyr Phe
                    210                   215                   220

Arg Glu Tyr Glu Gly Glu Thr Glu Glu Arg Arg Arg Leu Arg Gln Glu
225                   230                   235                   240

Asn Gly Thr Val His Ala Ile Ala
                    245

<210> SEQ ID NO 4
<211> LENGTH: 81
<212> TYPE: PRT
<213> ORGANISM: Mus musculus

<400> SEQUENCE: 4

Val Ile Lys Pro Lys Lys Asn Lys Thr Glu Gly Glu Lys Ser Thr Glu
1               5                   10                  15

Lys Pro Lys Arg Lys Lys Lys Gly Gly Lys Asn Gly Lys Gly Arg Arg
                    20                  25                  30

Asn Lys Lys Lys Lys Asn Pro Cys Thr Ala Lys Phe Gln Asn Phe Cys
                35                  40                  45

Ile His Gly Glu Cys Arg Tyr Ile Glu Asn Leu Glu Val Val Thr Cys
        50                  55                  60

Asn Cys His Gln Asp Tyr Phe Gly Glu Arg Cys Gly Glu Lys Ser Met
65                  70                  75                  80

Lys

<210> SEQ ID NO 5
<211> LENGTH: 243
<212> TYPE: PRT
<213> ORGANISM: Rattus norvegicus

<400> SEQUENCE: 5

Met Arg Thr Pro Ser Leu Ser Leu Ala Leu Ser Val Leu Ser Leu Leu
1               5                   10                  15

Val Leu Gly Ser Gly His Tyr Ala Ala Gly Leu Glu Leu Asn Gly Thr
                    20                  25                  30

Ser Ser Gly Lys Gly Glu Pro Ser Ser Gly Asp His Ser Ala Gly Gly
            35                  40                  45

Leu Val Val Ser Glu Val Ser Thr Ile Ser Glu Met Pro Ser Gly Ser
        50                  55                  60
```

-continued

```
Glu Leu Ser Thr Gly Asp Tyr Asp Tyr Ser Glu Glu Tyr Asp Asn Glu
65                  70                  75                  80

Pro Gln Ile Ser Gly Tyr Ile Val Asp Asp Ser Val Arg Val Glu Gln
                85                  90                  95

Val Ile Lys Pro Lys Glu Asn Lys Thr Glu Gly Glu Lys Ser Ser Glu
            100                 105                 110

Lys Pro Lys Arg Lys Lys Lys Gly Gly Lys Gly Gly Lys Gly Arg Arg
        115                 120                 125

Asn Arg Lys Lys Lys Lys Asn Pro Cys Ala Ala Lys Phe Gln Asn Phe
    130                 135                 140

Cys Ile His Gly Glu Cys Arg Tyr Ile Glu Asn Leu Glu Val Val Thr
145                 150                 155                 160

Cys His Cys His Gln Asp Tyr Phe Gly Glu Arg Cys Gly Glu Lys Thr
                165                 170                 175

Met Lys Thr Gln Lys Lys Asp Asp Ser Asp Leu Ser Lys Ile Ala Leu
            180                 185                 190

Ala Ala Ile Ile Val Phe Val Ser Ala Val Ser Val Ala Ala Ile Gly
        195                 200                 205

Ile Ile Thr Ala Val Leu Leu Arg Lys Arg Phe Phe Arg Glu Tyr Glu
    210                 215                 220

Glu Ala Glu Glu Arg Arg Arg Leu Arg Gln Glu Asn Gly Thr Ala His
225                 230                 235                 240

Ala Ile Ala
```

```
<210> SEQ ID NO 6
<211> LENGTH: 82
<212> TYPE: PRT
<213> ORGANISM: Rattus norvegicus

<400> SEQUENCE: 6
```

```
Val Ile Lys Pro Lys Glu Asn Lys Thr Glu Gly Glu Lys Ser Ser Glu
1                   5                   10                  15

Lys Pro Lys Arg Lys Lys Lys Gly Gly Lys Gly Gly Lys Gly Arg Arg
                20                  25                  30

Asn Arg Lys Lys Lys Lys Asn Pro Cys Ala Ala Lys Phe Gln Asn Phe
            35                  40                  45

Cys Ile His Gly Glu Cys Arg Tyr Ile Glu Asn Leu Glu Val Val Thr
        50                  55                  60

Cys His Cys His Gln Asp Tyr Phe Gly Glu Arg Cys Gly Glu Lys Thr
65                  70                  75                  80

Met Lys
```

```
<210> SEQ ID NO 7
<211> LENGTH: 1210
<212> TYPE: PRT
<213> ORGANISM: Homo sapiens

<400> SEQUENCE: 7
```

```
Met Arg Pro Ser Gly Thr Ala Gly Ala Ala Leu Leu Ala Leu Leu Ala
1                   5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
```

-continued

```
          50                      55                      60

Leu Glu Ile Thr Tyr Val Gln Arg Asn Tyr Asp Leu Ser Phe Leu Lys
65                      70                      75                      80

Thr Ile Gln Glu Val Ala Gly Tyr Val Leu Ile Ala Leu Asn Thr Val
                        85                      90                      95

Glu Arg Ile Pro Leu Glu Asn Leu Gln Ile Ile Arg Gly Asn Met Tyr
                        100                     105                     110

Tyr Glu Asn Ser Tyr Ala Leu Ala Val Leu Ser Asn Tyr Asp Ala Asn
            115                     120                     125

Lys Thr Gly Leu Lys Glu Leu Pro Met Arg Asn Leu Gln Glu Ile Leu
            130                     135                     140

His Gly Ala Val Arg Phe Ser Asn Asn Pro Ala Leu Cys Asn Val Glu
145                     150                     155                     160

Ser Ile Gln Trp Arg Asp Ile Val Ser Ser Asp Phe Leu Ser Asn Met
                        165                     170                     175

Ser Met Asp Phe Gln Asn His Leu Gly Ser Cys Gln Lys Cys Asp Pro
                        180                     185                     190

Ser Cys Pro Asn Gly Ser Cys Trp Gly Ala Gly Glu Glu Asn Cys Gln
            195                     200                     205

Lys Leu Thr Lys Ile Ile Cys Ala Gln Gln Cys Ser Gly Arg Cys Arg
            210                     215                     220

Gly Lys Ser Pro Ser Asp Cys Cys His Asn Gln Cys Ala Ala Gly Cys
225                     230                     235                     240

Thr Gly Pro Arg Glu Ser Asp Cys Leu Val Cys Arg Lys Phe Arg Asp
                        245                     250                     255

Glu Ala Thr Cys Lys Asp Thr Cys Pro Pro Leu Met Leu Tyr Asn Pro
                        260                     265                     270

Thr Thr Tyr Gln Met Asp Val Asn Pro Glu Gly Lys Tyr Ser Phe Gly
                        275                     280                     285

Ala Thr Cys Val Lys Lys Cys Pro Arg Asn Tyr Val Val Thr Asp His
            290                     295                     300

Gly Ser Cys Val Arg Ala Cys Gly Ala Asp Ser Tyr Glu Met Glu Glu
305                     310                     315                     320

Asp Gly Val Arg Lys Cys Lys Lys Cys Glu Gly Pro Cys Arg Lys Val
                        325                     330                     335

Cys Asn Gly Ile Gly Ile Gly Glu Phe Lys Asp Ser Leu Ser Ile Asn
            340                     345                     350

Ala Thr Asn Ile Lys His Phe Lys Asn Cys Thr Ser Ile Ser Gly Asp
            355                     360                     365

Leu His Ile Leu Pro Val Ala Phe Arg Gly Asp Ser Phe Thr His Thr
            370                     375                     380

Pro Pro Leu Asp Pro Gln Glu Leu Asp Ile Leu Lys Thr Val Lys Glu
385                     390                     395                     400

Ile Thr Gly Phe Leu Leu Ile Gln Ala Trp Pro Glu Asn Arg Thr Asp
                        405                     410                     415

Leu His Ala Phe Glu Asn Leu Glu Ile Ile Arg Gly Arg Thr Lys Gln
            420                     425                     430

His Gly Gln Phe Ser Leu Ala Val Val Ser Leu Asn Ile Thr Ser Leu
            435                     440                     445

Gly Leu Arg Ser Leu Lys Glu Ile Ser Asp Gly Asp Val Ile Ile Ser
            450                     455                     460

Gly Asn Lys Asn Leu Cys Tyr Ala Asn Thr Ile Asn Trp Lys Lys Leu
465                     470                     475                     480
```

```
Phe Gly Thr Ser Gly Gln Lys Thr Lys Ile Ile Ser Asn Arg Gly Glu
            485             490             495

Asn Ser Cys Lys Ala Thr Gly Gln Val Cys His Ala Leu Cys Ser Pro
            500             505             510

Glu Gly Cys Trp Gly Pro Glu Pro Arg Asp Cys Val Ser Cys Arg Asn
            515             520             525

Val Ser Arg Gly Arg Glu Cys Val Asp Lys Cys Asn Leu Leu Glu Gly
            530             535             540

Glu Pro Arg Glu Phe Val Glu Asn Ser Glu Cys Ile Gln Cys His Pro
545             550             555             560

Glu Cys Leu Pro Gln Ala Met Asn Ile Thr Cys Thr Gly Arg Gly Pro
            565             570             575

Asp Asn Cys Ile Gln Cys Ala His Tyr Ile Asp Gly Pro His Cys Val
            580             585             590

Lys Thr Cys Pro Ala Gly Val Met Gly Glu Asn Asn Thr Leu Val Trp
            595             600             605

Lys Tyr Ala Asp Ala Gly His Val Cys His Leu Cys His Pro Asn Cys
            610             615             620

Thr Tyr Gly Cys Thr Gly Pro Gly Leu Glu Gly Cys Pro Thr Asn Gly
625             630             635             640

Pro Lys Ile Pro Ser Ile Ala Thr Gly Met Val Gly Ala Leu Leu Leu
            645             650             655

Leu Leu Val Val Ala Leu Gly Ile Gly Leu Phe Met Arg Arg Arg His
            660             665             670

Ile Val Arg Lys Arg Thr Leu Arg Arg Leu Leu Gln Glu Arg Glu Leu
            675             680             685

Val Glu Pro Leu Thr Pro Ser Gly Glu Ala Pro Asn Gln Ala Leu Leu
            690             695             700

Arg Ile Leu Lys Glu Thr Glu Phe Lys Lys Ile Lys Val Leu Gly Ser
705             710             715             720

Gly Ala Phe Gly Thr Val Tyr Lys Gly Leu Trp Ile Pro Glu Gly Glu
            725             730             735

Lys Val Lys Ile Pro Val Ala Ile Lys Glu Leu Arg Glu Ala Thr Ser
            740             745             750

Pro Lys Ala Asn Lys Glu Ile Leu Asp Glu Ala Tyr Val Met Ala Ser
            755             760             765

Val Asp Asn Pro His Val Cys Arg Leu Leu Gly Ile Cys Leu Thr Ser
            770             775             780

Thr Val Gln Leu Ile Thr Gln Leu Met Pro Phe Gly Cys Leu Leu Asp
785             790             795             800

Tyr Val Arg Glu His Lys Asp Asn Ile Gly Ser Gln Tyr Leu Leu Asn
            805             810             815

Trp Cys Val Gln Ile Ala Lys Gly Met Asn Tyr Leu Glu Asp Arg Arg
            820             825             830

Leu Val His Arg Asp Leu Ala Ala Arg Asn Val Leu Val Lys Thr Pro
            835             840             845

Gln His Val Lys Ile Thr Asp Phe Gly Leu Ala Lys Leu Leu Gly Ala
            850             855             860

Glu Glu Lys Glu Tyr His Ala Glu Gly Gly Lys Val Pro Ile Lys Trp
865             870             875             880

Met Ala Leu Glu Ser Ile Leu His Arg Ile Tyr Thr His Gln Ser Asp
            885             890             895
```

-continued

```
Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
        930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
            965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
            995                 1000                1005

Asp Val  Val Asp Ala Asp Glu  Tyr Leu Ile Pro Gln  Gln Gly Phe
        1010                1015                1020

Phe Ser  Ser Pro Ser Thr Ser  Arg Thr Pro Leu Leu  Ser Ser Leu
        1025                1030                1035

Ser Ala  Thr Ser Asn Asn Ser  Thr Val Ala Cys Ile  Asp Arg Asn
        1040                1045                1050

Gly Leu  Gln Ser Cys Pro Ile  Lys Glu Asp Ser Phe  Leu Gln Arg
        1055                1060                1065

Tyr Ser  Ser Asp Pro Thr Gly  Ala Leu Thr Glu Asp  Ser Ile Asp
        1070                1075                1080

Asp Thr  Phe Leu Pro Val Pro  Glu Tyr Ile Asn Gln  Ser Val Pro
        1085                1090                1095

Lys Arg  Pro Ala Gly Ser Val  Gln Asn Pro Val Tyr  His Asn Gln
        1100                1105                1110

Pro Leu  Asn Pro Ala Pro Ser  Arg Asp Pro His Tyr  Gln Asp Pro
        1115                1120                1125

His Ser  Thr Ala Val Gly Asn  Pro Glu Tyr Leu Asn  Thr Val Gln
        1130                1135                1140

Pro Thr  Cys Val Asn Ser Thr  Phe Asp Ser Pro Ala  His Trp Ala
        1145                1150                1155

Gln Lys  Gly Ser His Gln Ile  Ser Leu Asp Asn Pro  Asp Tyr Gln
        1160                1165                1170

Gln Asp  Phe Phe Pro Lys Glu  Ala Lys Pro Asn Gly  Ile Phe Lys
        1175                1180                1185

Gly Ser  Thr Ala Glu Asn Ala  Glu Tyr Leu Arg Val  Ala Pro Gln
        1190                1195                1200

Ser Ser  Glu Phe Ile Gly Ala
        1205                1210
```

<210> SEQ ID NO 8
<211> LENGTH: 1210
<212> TYPE: PRT
<213> ORGANISM: Mus musculus

<400> SEQUENCE: 8

```
Met Arg Pro Ser Gly Thr Ala Arg Thr Thr Leu Leu Val Leu Leu Thr
1               5                   10                  15

Ala Leu Cys Ala Ala Gly Gly Ala Leu Glu Glu Lys Lys Val Cys Gln
            20                  25                  30

Gly Thr Ser Asn Arg Leu Thr Gln Leu Gly Thr Phe Glu Asp His Phe
        35                  40                  45
```

-continued

```
Leu Ser Leu Gln Arg Met Tyr Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Ala Leu
                100                 105                 110

Tyr Glu Asn Thr Tyr Ala Leu Ala Ile Leu Ser Asn Tyr Gly Thr Asn
            115                 120                 125

Arg Thr Gly Leu Arg Glu Leu Pro Met Arg Asn Leu Gln Glu Ile Leu
    130                 135                 140

Ile Gly Ala Val Arg Phe Ser Asn Asn Pro Ile Leu Cys Asn Met Asp
145                 150                 155                 160

Thr Ile Gln Trp Arg Asp Ile Val Gln Asn Val Phe Met Ser Asn Met
                165                 170                 175

Ser Met Asp Leu Gln Ser His Pro Ser Ser Cys Pro Lys Cys Asp Pro
            180                 185                 190

Ser Cys Pro Asn Gly Ser Cys Trp Gly Gly Gly Glu Glu Asn Cys Gln
            195                 200                 205

Lys Leu Thr Lys Ile Ile Cys Ala Gln Gln Cys Ser His Arg Cys Arg
    210                 215                 220

Gly Arg Ser Pro Ser Asp Cys Cys His Asn Gln Cys Ala Ala Gly Cys
225                 230                 235                 240

Thr Gly Pro Arg Glu Ser Asp Cys Leu Val Cys Gln Lys Phe Gln Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Pro Asp Tyr Tyr Glu Val Glu Glu
305                 310                 315                 320

Asp Gly Ile Arg Lys Cys Lys Lys Cys Asp Gly Pro Cys Arg Lys Val
            325                 330                 335

Cys Asn Gly Ile Gly Ile Gly Glu Phe Lys Asp Thr Leu Ser Ile Asn
            340                 345                 350

Ala Thr Asn Ile Lys His Phe Lys Tyr Cys Thr Ala Ile Ser Gly Asp
        355                 360                 365

Leu His Ile Leu Pro Val Ala Phe Lys Gly Asp Ser Phe Thr Arg Thr
    370                 375                 380

Pro Pro Leu Asp Pro Arg Glu Leu Glu Ile Leu Lys Thr Val Lys Glu
385                 390                 395                 400

Ile Thr Gly Phe Leu Leu Ile Gln Ala Trp Pro Asp Asn Trp Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Gly Leu Asn Ile Thr Ser Leu
            435                 440                 445

Gly Leu Arg Ser Leu Lys Glu Ile Ser Asp Gly Asp Val Ile Ile Ser
    450                 455                 460
```

```
Gly Asn Arg Asn Leu Cys Tyr Ala Asn Thr Ile Asn Trp Lys Lys Leu
465             470                 475                 480

Phe Gly Thr Pro Asn Gln Lys Thr Lys Ile Met Asn Asn Arg Ala Glu
                485                 490                 495

Lys Asp Cys Lys Ala Val Asn His Val Cys Asn Pro Leu Cys Ser Ser
            500                 505                 510

Glu Gly Cys Trp Gly Pro Glu Pro Arg Asp Cys Val Ser Cys Gln Asn
        515                 520                 525

Val Ser Arg Gly Arg Glu Cys Val Glu Lys Cys Asn Ile Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Ile Met Gly Glu Asn Asn Thr Leu Val Trp
            595                 600                 605

Lys Tyr Ala Asp Ala Asn Asn Val Cys His Leu Cys His Ala Asn Cys
    610                 615                 620

Thr Tyr Gly Cys Ala Gly Pro Gly Leu Gln Gly Cys Glu Val Trp Pro
625                 630                 635                 640

Ser Gly Pro Lys Ile Pro Ser Ile Ala Thr Gly Ile Val Gly Gly Leu
                645                 650                 655

Leu Phe Ile Val Val Val Ala Leu Gly Ile Gly Leu Phe Met Arg Arg
            660                 665                 670

Arg His Ile Val Arg Lys Arg Thr Leu Arg Arg Leu Leu Gln Glu Arg
            675                 680                 685

Glu Leu Val Glu Pro Leu Thr Pro Ser Gly Glu Ala Pro Asn Gln Ala
    690                 695                 700

His Leu Arg Ile Leu Lys Glu Thr Glu Phe Lys Lys Ile Lys Val Leu
705                 710                 715                 720

Gly Ser Gly Ala Phe Gly Thr Val Tyr Lys Gly Leu Trp Ile Pro Glu
                725                 730                 735

Gly Glu Lys Val Lys Ile Pro Val Ala Ile Lys Glu Leu Arg Glu Ala
            740                 745                 750

Thr Ser Pro Lys Ala Asn Lys Glu Ile Leu Asp Glu Ala Tyr Val Met
            755                 760                 765

Ala Ser Val Asp Asn Pro His Val Cys Arg Leu Leu Gly Ile Cys Leu
    770                 775                 780

Thr Ser Thr Val Gln Leu Ile Thr Gln Leu Met Pro Tyr Gly Cys Leu
785                 790                 795                 800

Leu Asp Tyr Val Arg Glu His Lys Asp Asn Ile Gly Ser Gln Tyr Leu
                805                 810                 815

Leu Asn Trp Cys Val Gln Ile Ala Lys Gly Met Asn Tyr Leu Glu Asp
            820                 825                 830

Arg Arg Leu Val His Arg Asp Leu Ala Ala Arg Asn Val Leu Val Lys
            835                 840                 845

Thr Pro Gln His Val Lys Ile Thr Asp Phe Gly Leu Ala Lys Leu Leu
    850                 855                 860

Gly Ala Glu Glu Lys Glu Tyr His Ala Glu Gly Gly Lys Val Pro Ile
865                 870                 875                 880

Lys Trp Met Ala Leu Glu Ser Ile Leu His Arg Ile Tyr Thr His Gln
```

-continued

```
              885            890                895

Ser Asp Val Trp Ser Tyr Gly Val Thr Val Trp Glu Leu Met Thr Phe
            900              905              910

Gly Ser Lys Pro Tyr Asp Gly Ile Pro Ala Ser Asp Ile Ser Ser Ile
            915              920              925

Leu Glu Lys Gly Glu Arg Leu Pro Gln Pro Ile Cys Thr Ile Asp
    930              935              940

Val Tyr Met Ile Met Val Lys Cys Trp Met Ile Asp Ala Asp Ser Arg
945              950              955              960

Pro Lys Phe Arg Glu Leu Ile Leu Glu Phe Ser Lys Met Ala Arg Asp
                965              970              975

Pro Gln Arg Tyr Leu Val Ile Gln Gly Asp Glu Arg Met His Leu Pro
            980              985              990

Ser Pro Thr Asp Ser Asn Phe Tyr Arg Ala Leu Met Asp Glu Glu Asp
            995              1000             1005

Met Glu Asp Val Val Asp Ala Asp Glu Tyr Leu Ile Pro Gln Gln
    1010             1015             1020

Gly Phe Phe Asn Ser Pro Ser Thr Ser Arg Thr Pro Leu Leu Ser
    1025             1030             1035

Ser Leu Ser Ala Thr Ser Asn Asn Ser Thr Val Ala Cys Ile Asn
    1040             1045             1050

Arg Asn Gly Ser Cys Arg Val Lys Glu Asp Ala Phe Leu Gln Arg
    1055             1060             1065

Tyr Ser Ser Asp Pro Thr Gly Ala Val Thr Glu Asp Asn Ile Asp
    1070             1075             1080

Asp Ala Phe Leu Pro Val Pro Glu Tyr Val Asn Gln Ser Val Pro
    1085             1090             1095

Lys Arg Pro Ala Gly Ser Val Gln Asn Pro Val Tyr His Asn Gln
    1100             1105             1110

Pro Leu His Pro Ala Pro Gly Arg Asp Leu His Tyr Gln Asn Pro
    1115             1120             1125

His Ser Asn Ala Val Gly Asn Pro Glu Tyr Leu Asn Thr Ala Gln
    1130             1135             1140

Pro Thr Cys Leu Ser Ser Gly Phe Asn Ser Pro Ala Leu Trp Ile
    1145             1150             1155

Gln Lys Gly Ser His Gln Met Ser Leu Asp Asn Pro Asp Tyr Gln
    1160             1165             1170

Gln Asp Phe Phe Pro Lys Glu Thr Lys Pro Asn Gly Ile Phe Lys
    1175             1180             1185

Gly Pro Thr Ala Glu Asn Ala Glu Tyr Leu Arg Val Ala Pro Pro
    1190             1195             1200

Ser Ser Glu Phe Ile Gly Ala
    1205             1210

<210> SEQ ID NO 9
<211> LENGTH: 1209
<212> TYPE: PRT
<213> ORGANISM: Rattus norvegicus

<400> SEQUENCE: 9

Met Arg Pro Ser Gly Thr Ala Arg Thr Lys Leu Leu Leu Leu Leu Ala
1               5                10               15

Ala Leu Cys Ala Ala Gly Gly Ala Leu Glu Glu Lys Lys Val Cys Gln
            20               25               30
```

```
Gly Thr Ser Asn Arg Leu Thr Gln Leu Gly Thr Phe Glu Asp His Phe
    35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Ala Leu
                100                 105                 110

Tyr Glu Asn Thr Tyr Ala Leu Ala Val Leu Ser Asn Tyr Gly Thr Asn
                115                 120                 125

Lys Thr Gly Leu Arg Glu Leu Pro Met Arg Asn Leu Gln Glu Ile Leu
    130                 135                 140

Ile Gly Ala Val Arg Phe Ser Asn Asn Pro Ile Leu Cys Asn Met Glu
145                 150                 155                 160

Thr Ile Gln Trp Arg Asp Ile Val Gln Asp Val Phe Leu Ser Asn Met
                165                 170                 175

Ser Met Asp Val Gln Arg His Leu Thr Gly Cys Pro Lys Cys Asp Pro
            180                 185                 190

Ser Cys Pro Asn Gly Ser Cys Trp Gly Arg Gly Glu Glu Asn Cys Gln
            195                 200                 205

Lys Leu Thr Lys Ile Ile Cys Ala Gln Gln Cys Ser Arg Arg Cys Arg
        210                 215                 220

Gly Arg Ser Pro Ser Asp Cys Cys His Asn Gln Cys Ala Ala Gly Cys
225                 230                 235                 240

Thr Gly Pro Arg Glu Ser Asp Cys Leu Val Cys His Arg Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Pro Asp Tyr Tyr Glu Val Glu Glu
305                 310                 315                 320

Asp Gly Val Ser Lys Cys Lys Lys Cys Asp Gly Pro Cys Arg Lys Val
                325                 330                 335

Cys Asn Gly Ile Gly Ile Gly Glu Phe Lys Asp Thr Leu Ser Ile Asn
            340                 345                 350

Ala Thr Asn Ile Lys His Phe Lys Tyr Cys Thr Ala Ile Ser Gly Asp
            355                 360                 365

Leu His Ile Leu Pro Val Ala Phe Lys Gly Asp Ser Phe Thr Arg Thr
    370                 375                 380

Pro Pro Leu Asp Pro Arg Glu Leu Glu Ile Leu Lys Thr Val Lys Glu
385                 390                 395                 400

Ile Thr Gly Phe Leu Leu Ile Gln Ala Trp Pro Glu Asn Trp Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Gly Leu Asn Ile Thr Ser Leu
    435                 440                 445

Gly Leu Arg Ser Leu Lys Glu Ile Ser Asp Gly Asp Val Ile Ile Ser
```

-continued

```
              450              455              460

Gly Asn Arg Asn Leu Cys Tyr Ala Asn Thr Ile Asn Trp Lys Lys Leu
465              470              475              480

Phe Gly Thr Pro Asn Gln Lys Thr Lys Ile Met Asn Asn Arg Ala Glu
                 485              490              495

Lys Asp Cys Lys Ala Thr Asn His Val Cys Asn Pro Leu Cys Ser Ser
                 500              505              510

Glu Gly Cys Trp Gly Pro Glu Pro Thr Asp Cys Val Ser Cys Gln Asn
                 515              520              525

Val Ser Arg Gly Arg Glu Cys Val Asp Lys Cys Asn Ile Leu Glu Gly
                 530              535              540

Glu Pro Arg Glu Phe Val Glu Asn Ser Glu Cys Ile Gln Cys His Pro
545              550              555              560

Glu Cys Leu Pro Gln Thr Met Asn Ile Thr Cys Thr Gly Arg Gly Pro
                 565              570              575

Asp Asn Cys Ile Lys Cys Ala His Tyr Val Asp Gly Pro His Cys Val
                 580              585              590

Lys Thr Cys Pro Ser Gly Ile Met Gly Glu Asn Asn Thr Leu Val Trp
                 595              600              605

Lys Phe Ala Asp Ala Asn Asn Val Cys His Leu Cys His Ala Asn Cys
                 610              615              620

Thr Tyr Gly Cys Ala Gly Pro Gly Leu Lys Gly Cys Gln Gln Pro Glu
625              630              635              640

Gly Pro Lys Ile Pro Ser Ile Ala Thr Gly Ile Val Gly Gly Leu Leu
                 645              650              655

Phe Ile Ile Val Val Ala Leu Gly Ile Gly Leu Phe Met Arg Arg Arg
                 660              665              670

His Ile Val Arg Lys Arg Thr Leu Arg Arg Leu Leu Gln Glu Arg Glu
                 675              680              685

Leu Val Glu Pro Leu Thr Pro Ser Gly Glu Ala Pro Asn Gln Ala His
                 690              695              700

Leu Arg Ile Leu Lys Glu Thr Lys Phe Lys Lys Ile Lys Val Leu Gly
705              710              715              720

Ser Gly Ala Phe Gly Thr Val Tyr Lys Gly Leu Trp Ile Pro Glu Gly
                 725              730              735

Glu Lys Val Lys Ile Pro Val Ala Ile Lys Glu Leu Arg Glu Ala Thr
                 740              745              750

Ser Pro Lys Ala Asn Lys Glu Ile Leu Asp Glu Ala Tyr Val Met Ala
                 755              760              765

Ser Val Asp Asn Pro His Val Cys Arg Leu Leu Gly Ile Cys Leu Thr
                 770              775              780

Ser Thr Val Gln Leu Ile Thr Gln Leu Met Pro Tyr Gly Cys Leu Leu
785              790              795              800

Asp Tyr Val Arg Glu His Lys Asp Asn Ile Gly Ser Gln Tyr Leu Leu
                 805              810              815

Asn Trp Cys Val Gln Ile Ala Lys Gly Met Asn Tyr Leu Glu Asp Arg
                 820              825              830

Arg Leu Val His Arg Asp Leu Ala Ala Arg Asn Val Leu Val Lys Thr
                 835              840              845

Pro Gln His Val Lys Ile Thr Asp Phe Gly Leu Ala Lys Leu Leu Gly
                 850              855              860

Ala Glu Glu Lys Glu Tyr His Ala Glu Gly Gly Lys Val Pro Ile Lys
865              870              875              880
```

-continued

```
Trp Met Ala Leu Glu Ser Ile Leu His Arg Ile Tyr Thr His Gln Ser
            885                 890                 895

Asp Val Trp Ser Tyr Gly Val Thr Val Trp Glu Leu Met Thr Phe Gly
            900                 905                 910

Ser Lys Pro Tyr Asp Gly Ile Pro Ala Ser Glu Ile Ser Ser Ile Leu
            915                 920                 925

Glu Lys Gly Glu Arg Leu Pro Gln Pro Pro Ile Cys Thr Ile Asp Val
        930                 935                 940

Tyr Met Ile Met Val Lys Cys Trp Met Ile Asp Ala Asp Ser Arg Pro
945                 950                 955                 960

Lys Phe Arg Glu Leu Ile Leu Glu Phe Ser Lys Met Ala Arg Asp Pro
                965                 970                 975

Gln Arg Tyr Leu Val Ile Gln Gly Asp Glu Arg Met His Leu Pro Ser
                980                 985                 990

Pro Thr Asp Ser Asn Phe Tyr Arg  Ala Leu Met Glu Glu  Glu Asp Met
            995                 1000                1005

Glu Asp  Val Val Asp Ala Asp  Glu Tyr Leu Ile Pro  Gln Gln Gly
    1010                1015                1020

Phe Phe  Asn Ser Pro Ser Thr  Ser Arg Thr Pro Leu  Leu Ser Ser
    1025                1030                1035

Leu Ser  Ala Asn Ser Asn Ser  Ser Thr Val Ala Cys  Ile Asn Arg
    1040                1045                1050

Asn Gly  Ser Cys Arg Val Lys  Glu Asp Ala Phe Leu  Gln Arg Tyr
    1055                1060                1065

Ser Ser  Asp Pro Thr Ser Val  Leu Thr Glu Asp Asn  Ile Asp Asp
    1070                1075                1080

Thr Phe  Leu Pro Val Pro Glu  Tyr Ile Asn Gln Ser  Val Pro Lys
    1085                1090                1095

Arg Pro  Ala Gly Ser Val Gln  Asn Pro Val Tyr His  Asn Gln Pro
    1100                1105                1110

Leu His  Pro Ala Pro Gly Arg  Asp Leu His Tyr Gln  Asn Pro His
    1115                1120                1125

Ser Asn  Ala Val Ser Asn Pro  Glu Tyr Leu Asn Thr  Ala Gln Pro
    1130                1135                1140

Thr Cys  Leu Ser Ser Gly Phe  Asp Ser Ser Ala Leu  Trp Ile Gln
    1145                1150                1155

Lys Gly  Ser His Gln Met Ser  Leu Asp Asn Pro Asp  Tyr Gln Gln
    1160                1165                1170

Asp Phe  Phe Pro Lys Glu Ala  Lys Pro Asn Gly Ile  Phe Lys Gly
    1175                1180                1185

Pro Thr  Ala Glu Asn Ala Glu  Tyr Leu Arg Val Ala  Pro Pro Ser
    1190                1195                1200

Ser Glu  Phe Ile Gly Ala
    1205
```

```
<210> SEQ ID NO 10
<211> LENGTH: 1255
<212> TYPE: PRT
<213> ORGANISM: Homo sapiens

<400> SEQUENCE: 10

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
```

-continued

```
                20               25               30
Leu Arg Leu Pro Ala Ser Pro Glu Thr His Leu Asp Met Leu Arg His
        35               40               45
Leu Tyr Gln Gly Cys Gln Val Val Gln Gly Asn Leu Glu Leu Thr Tyr
    50               55               60
Leu Pro Thr Asn Ala Ser Leu Ser Phe Leu Gln Asp Ile Gln Glu Val
65               70               75               80
Gln Gly Tyr Val Leu Ile Ala His Asn Gln Val Arg Gln Val Pro Leu
                85               90               95
Gln Arg Leu Arg Ile Val Arg Gly Thr Gln Leu Phe Glu Asp Asn Tyr
        100              105              110
Ala Leu Ala Val Leu Asp Asn Gly Asp Pro Leu Asn Asn Thr Thr Pro
        115              120              125
Val Thr Gly Ala Ser Pro Gly Gly Leu Arg Glu Leu Gln Leu Arg Ser
        130              135              140
Leu Thr Glu Ile Leu Lys Gly Gly Val Leu Ile Gln Arg Asn Pro Gln
145              150              155              160
Leu Cys Tyr Gln Asp Thr Ile Leu Trp Lys Asp Ile Phe His Lys Asn
        165              170              175
Asn Gln Leu Ala Leu Thr Leu Ile Asp Thr Asn Arg Ser Arg Ala Cys
        180              185              190
His Pro Cys Ser Pro Met Cys Lys Gly Ser Arg Cys Trp Gly Glu Ser
        195              200              205
Ser Glu Asp Cys Gln Ser Leu Thr Arg Thr Val Cys Ala Gly Gly Cys
    210              215              220
Ala Arg Cys Lys Gly Pro Leu Pro Thr Asp Cys Cys His Glu Gln Cys
225              230              235              240
Ala Ala Gly Cys Thr Gly Pro Lys His Ser Asp Cys Leu Ala Cys Leu
        245              250              255
His Phe Asn His Ser Gly Ile Cys Glu Leu His Cys Pro Ala Leu Val
        260              265              270
Thr Tyr Asn Thr Asp Thr Phe Glu Ser Met Pro Asn Pro Glu Gly Arg
        275              280              285
Tyr Thr Phe Gly Ala Ser Cys Val Thr Ala Cys Pro Tyr Asn Tyr Leu
    290              295              300
Ser Thr Asp Val Gly Ser Cys Thr Leu Val Cys Pro Leu His Asn Gln
305              310              315              320
Glu Val Thr Ala Glu Asp Gly Thr Gln Arg Cys Glu Lys Cys Ser Lys
        325              330              335
Pro Cys Ala Arg Val Cys Tyr Gly Leu Gly Met Glu His Leu Arg Glu
        340              345              350
Val Arg Ala Val Thr Ser Ala Asn Ile Gln Glu Phe Ala Gly Cys Lys
        355              360              365
Lys Ile Phe Gly Ser Leu Ala Phe Leu Pro Glu Ser Phe Asp Gly Asp
    370              375              380
Pro Ala Ser Asn Thr Ala Pro Leu Gln Pro Glu Gln Leu Gln Val Phe
385              390              395              400
Glu Thr Leu Glu Glu Ile Thr Gly Tyr Leu Tyr Ile Ser Ala Trp Pro
            405              410              415
Asp Ser Leu Pro Asp Leu Ser Val Phe Gln Asn Leu Gln Val Ile Arg
        420              425              430
Gly Arg Ile Leu His Asn Gly Ala Tyr Ser Leu Thr Leu Gln Gly Leu
        435              440              445
```

-continued

```
Gly Ile Ser Trp Leu Gly Leu Arg Ser Leu Arg Glu Leu Gly Ser Gly
    450             455             460

Leu Ala Leu Ile His His Asn Thr His Leu Cys Phe Val His Thr Val
465             470             475             480

Pro Trp Asp Gln Leu Phe Arg Asn Pro His Gln Ala Leu Leu His Thr
                485             490             495

Ala Asn Arg Pro Glu Asp Glu Cys Val Gly Glu Gly Leu Ala Cys His
            500             505             510

Gln Leu Cys Ala Arg Gly His Cys Trp Gly Pro Gly Pro Thr Gln Cys
        515             520             525

Val Asn Cys Ser Gln Phe Leu Arg Gly Gln Glu Cys Val Glu Glu Cys
    530             535             540

Arg Val Leu Gln Gly Leu Pro Arg Glu Tyr Val Asn Ala Arg His Cys
545             550             555             560

Leu Pro Cys His Pro Glu Cys Gln Pro Gln Asn Gly Ser Val Thr Cys
            565             570             575

Phe Gly Pro Glu Ala Asp Gln Cys Val Ala Cys Ala His Tyr Lys Asp
            580             585             590

Pro Pro Phe Cys Val Ala Arg Cys Pro Ser Gly Val Lys Pro Asp Leu
        595             600             605

Ser Tyr Met Pro Ile Trp Lys Phe Pro Asp Glu Glu Gly Ala Cys Gln
    610             615             620

Pro Cys Pro Ile Asn Cys Thr His Ser Cys Val Asp Leu Asp Asp Lys
625             630             635             640

Gly Cys Pro Ala Glu Gln Arg Ala Ser Pro Leu Thr Ser Ile Ile Ser
            645             650             655

Ala Val Val Gly Ile Leu Leu Val Val Val Leu Gly Val Val Phe Gly
            660             665             670

Ile Leu Ile Lys Arg Arg Gln Gln Lys Ile Arg Lys Tyr Thr Met Arg
    675             680             685

Arg Leu Leu Gln Glu Thr Glu Leu Val Glu Pro Leu Thr Pro Ser Gly
    690             695             700

Ala Met Pro Asn Gln Ala Gln Met Arg Ile Leu Lys Glu Thr Glu Leu
705             710             715             720

Arg Lys Val Lys Val Leu Gly Ser Gly Ala Phe Gly Thr Val Tyr Lys
            725             730             735

Gly Ile Trp Ile Pro Asp Gly Glu Asn Val Lys Ile Pro Val Ala Ile
            740             745             750

Lys Val Leu Arg Glu Asn Thr Ser Pro Lys Ala Asn Lys Glu Ile Leu
    755             760             765

Asp Glu Ala Tyr Val Met Ala Gly Val Gly Ser Pro Tyr Val Ser Arg
    770             775             780

Leu Leu Gly Ile Cys Leu Thr Ser Thr Val Gln Leu Val Thr Gln Leu
785             790             795             800

Met Pro Tyr Gly Cys Leu Leu Asp His Val Arg Glu Asn Arg Gly Arg
            805             810             815

Leu Gly Ser Gln Asp Leu Leu Asn Trp Cys Met Gln Ile Ala Lys Gly
        820             825             830

Met Ser Tyr Leu Glu Asp Val Arg Leu Val His Arg Asp Leu Ala Ala
    835             840             845

Arg Asn Val Leu Val Lys Ser Pro Asn His Val Lys Ile Thr Asp Phe
    850             855             860
```

-continued

```
Gly Leu Ala Arg Leu Leu Asp Ile Asp Glu Thr Glu Tyr His Ala Asp
865             870             875             880

Gly Gly Lys Val Pro Ile Lys Trp Met Ala Leu Glu Ser Ile Leu Arg
            885             890             895

Arg Arg Phe Thr His Gln Ser Asp Val Trp Ser Tyr Gly Val Thr Val
        900             905             910

Trp Glu Leu Met Thr Phe Gly Ala Lys Pro Tyr Asp Gly Ile Pro Ala
        915             920             925

Arg Glu Ile Pro Asp Leu Leu Glu Lys Gly Glu Arg Leu Pro Gln Pro
    930             935             940

Pro Ile Cys Thr Ile Asp Val Tyr Met Ile Met Val Lys Cys Trp Met
945             950             955             960

Ile Asp Ser Glu Cys Arg Pro Arg Phe Arg Glu Leu Val Ser Glu Phe
            965             970             975

Ser Arg Met Ala Arg Asp Pro Gln Arg Phe Val Val Ile Gln Asn Glu
            980             985             990

Asp Leu Gly Pro Ala Ser Pro Leu  Asp Ser Thr Phe Tyr  Arg Ser Leu
        995             1000            1005

Leu Glu  Asp Asp Asp Met Gly  Asp Leu Val Asp Ala  Glu Glu Tyr
    1010            1015            1020

Leu Val  Pro Gln Gln Gly Phe  Phe Cys Pro Asp Pro  Ala Pro Gly
    1025            1030            1035

Ala Gly  Gly Met Val His His  Arg His Arg Ser Ser  Ser Thr Arg
    1040            1045            1050

Ser Gly  Gly Gly Asp Leu Thr  Leu Gly Leu Glu Pro  Ser Glu Glu
    1055            1060            1065

Glu Ala  Pro Arg Ser Pro Leu  Ala Pro Ser Glu Gly  Ala Gly Ser
    1070            1075            1080

Asp Val  Phe Asp Gly Asp Leu  Gly Met Gly Ala Ala  Lys Gly Leu
    1085            1090            1095

Gln Ser  Leu Pro Thr His Asp  Pro Ser Pro Leu Gln  Arg Tyr Ser
    1100            1105            1110

Glu Asp  Pro Thr Val Pro Leu  Pro Ser Glu Thr Asp  Gly Tyr Val
    1115            1120            1125

Ala Pro  Leu Thr Cys Ser Pro  Gln Pro Glu Tyr Val  Asn Gln Pro
    1130            1135            1140

Asp Val  Arg Pro Gln Pro Pro  Ser Pro Arg Glu Gly  Pro Leu Pro
    1145            1150            1155

Ala Ala  Arg Pro Ala Gly Ala  Thr Leu Glu Arg Pro  Lys Thr Leu
    1160            1165            1170

Ser Pro  Gly Lys Asn Gly Val  Val Lys Asp Val Phe  Ala Phe Gly
    1175            1180            1185

Gly Ala  Val Glu Asn Pro Glu  Tyr Leu Thr Pro Gln  Gly Gly Ala
    1190            1195            1200

Ala Pro  Gln Pro His Pro Pro  Pro Ala Phe Ser Pro  Ala Phe Asp
    1205            1210            1215

Asn Leu  Tyr Tyr Trp Asp Gln  Asp Pro Pro Glu Arg  Gly Ala Pro
    1220            1225            1230

Pro Ser  Thr Phe Lys Gly Thr  Pro Thr Ala Glu Asn  Pro Glu Tyr
    1235            1240            1245

Leu Gly  Leu Asp Val Pro Val
    1250            1255
```

<210> SEQ ID NO 11
<211> LENGTH: 1256
<212> TYPE: PRT
<213> ORGANISM: Mus musculus

<400> SEQUENCE: 11

```
Met Glu Leu Ala Ala Trp Cys Arg Trp Gly Phe Leu Leu Ala Leu Leu
1               5                   10                  15

Ser Pro Gly Ala Ala Gly Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Ala Asn Ala Ser Leu Ser Phe Leu Gln Asp Ile Gln Glu Val
65                  70                  75                  80

Gln Gly Tyr Met Leu Ile Ala His Asn Arg Val Lys His Val Pro Leu
                85                  90                  95

Gln Arg Leu Arg Ile Val Arg Gly Thr Gln Leu Phe Glu Asp Lys Tyr
            100                 105                 110

Ala Leu Ala Val Leu Asp Asn Arg Asp Pro Leu Asp Asn Val Thr Thr
            115                 120                 125

Ala Ala Pro Gly Arg Thr Pro Glu Gly Leu Arg Glu Leu Gln Leu Arg
        130                 135                 140

Ser Leu Thr Glu Ile Leu Lys Gly Gly Val Leu Ile Arg Gly Asn Pro
145                 150                 155                 160

Gln Leu Cys Tyr Gln Asp Met Val Leu Trp Lys Asp Val Leu Arg Lys
                165                 170                 175

Asn Asn Gln Leu Ala Pro Val Asp Met Asp Thr Asn Arg Ser Arg Ala
            180                 185                 190

Cys Pro Pro Cys Ala Pro Thr Cys Lys Asp Asn His Cys Trp Gly Glu
            195                 200                 205

Ser Pro Glu Asp Cys Gln Ile Leu Thr Gly Thr Ile Cys Thr Ser Gly
        210                 215                 220

Cys Ala Arg Cys Lys Gly Arg Leu Pro Thr Asp Cys Cys His Glu Gln
225                 230                 235                 240

Cys Ala Ala Gly Cys Thr Gly Pro Lys His Ser Asp Cys Leu Ala Cys
                245                 250                 255

Leu His Phe Asn His Ser Gly Ile Cys Glu Leu His Cys Pro Ala Leu
            260                 265                 270

Ile Thr Tyr Asn Thr Asp Thr Phe Glu Ser Met Leu Asn Pro Glu Gly
        275                 280                 285

Arg Tyr Thr Phe Gly Ala Ser Cys Val Thr Thr Cys Pro Tyr Asn Tyr
        290                 295                 300

Leu Ser Thr Glu Val Gly Ser Cys Thr Leu Val Cys Pro Pro Asn Asn
305                 310                 315                 320

Gln Glu Val Thr Ala Glu Asp Gly Thr Gln Arg Cys Glu Lys Cys Ser
                325                 330                 335

Lys Pro Cys Ala Gly Val Cys Tyr Gly Leu Gly Met Glu His Leu Arg
            340                 345                 350

Gly Ala Arg Ala Ile Thr Ser Asp Asn Ile Gln Glu Phe Ala Gly Cys
            355                 360                 365

Lys Lys Ile Phe Gly Ser Leu Ala Phe Leu Pro Glu Ser Phe Asp Gly
        370                 375                 380
```

```
Asn Pro Ser Ser Gly Val Ala Pro Leu Lys Pro Glu His Leu Gln Val
385             390             395             400

Phe Glu Thr Leu Glu Glu Ile Thr Gly Tyr Leu Tyr Ile Ser Ala Trp
            405             410             415

Pro Glu Ser Phe Gln Asp Leu Ser Val Phe Gln Asn Leu Arg Val Ile
            420             425             430

Arg Gly Arg Ile Leu His Asp Gly Ala Tyr Ser Leu Thr Leu Gln Gly
            435             440             445

Leu Gly Ile His Ser Leu Gly Leu Arg Ser Leu Arg Glu Leu Gly Ser
            450             455             460

Gly Leu Ala Leu Ile His Arg Asn Thr His Leu Cys Phe Val Asn Thr
465             470             475             480

Val Pro Trp Asp Gln Leu Phe Arg Asn Pro His Gln Ala Leu Leu His
            485             490             495

Ser Gly Asn Arg Pro Glu Glu Ala Cys Gly Leu Glu Gly Leu Val Cys
            500             505             510

Asn Ser Leu Cys Ala Arg Gly His Cys Trp Gly Pro Gly Pro Thr Gln
            515             520             525

Cys Val Asn Cys Ser Gln Phe Leu Arg Gly Gln Glu Cys Val Glu Glu
            530             535             540

Cys Arg Val Trp Lys Gly Leu Pro Arg Glu Tyr Val Arg Gly Lys His
545             550             555             560

Cys Leu Pro Cys His Pro Glu Cys Gln Pro Gln Asn Ser Ser Glu Thr
            565             570             575

Cys Tyr Gly Ser Glu Ala Asp Gln Cys Glu Ala Cys Ala His Tyr Lys
            580             585             590

Asp Ser Ser Ser Cys Val Ala Arg Cys Pro Ser Gly Val Lys Pro Asp
            595             600             605

Leu Ser Tyr Met Pro Ile Trp Lys Tyr Pro Asp Glu Glu Gly Ile Cys
            610             615             620

Gln Pro Cys Pro Ile Asn Cys Thr His Ser Cys Val Asp Leu Asp Glu
625             630             635             640

Arg Gly Cys Pro Ala Glu Gln Arg Ala Ser Pro Val Thr Phe Ile Ile
            645             650             655

Ala Thr Val Val Gly Val Leu Leu Phe Leu Ile Ile Val Val Val Ile
            660             665             670

Gly Ile Leu Ile Lys Arg Arg Arg Gln Lys Ile Arg Lys Tyr Thr Met
            675             680             685

Arg Arg Leu Leu Gln Glu Thr Glu Leu Val Glu Pro Leu Thr Pro Ser
            690             695             700

Gly Ala Val Pro Asn Gln Ala Gln Met Arg Ile Leu Lys Glu Thr Glu
705             710             715             720

Leu Arg Lys Leu Lys Val Leu Gly Ser Gly Ala Phe Gly Thr Val Tyr
            725             730             735

Lys Gly Ile Trp Ile Pro Asp Gly Glu Asn Val Lys Ile Pro Val Ala
            740             745             750

Ile Lys Val Leu Arg Glu Asn Thr Ser Pro Lys Ala Asn Lys Glu Ile
            755             760             765

Leu Asp Glu Ala Tyr Val Met Ala Gly Val Gly Ser Pro Tyr Val Ser
            770             775             780

Arg Leu Leu Gly Ile Cys Leu Thr Ser Thr Val Gln Leu Val Thr Gln
785             790             795             800

Leu Met Pro Tyr Gly Cys Leu Leu Asp His Val Arg Glu His Arg Gly
```

-continued

```
                    805                  810                  815

Arg Leu Gly Ser Gln Asp Leu Leu Asn Trp Cys Val Gln Ile Ala Lys
            820                  825                  830

Gly Met Ser Tyr Leu Glu Glu Val Arg Leu Val His Arg Asp Leu Ala
            835                  840                  845

Ala Arg Asn Val Leu Val Lys Ser Pro Asn His Val Lys Ile Thr Asp
    850                  855                  860

Phe Gly Leu Ala Arg Leu Leu Asp Ile Asp Glu Thr Glu Tyr His Ala
865                  870                  875                  880

Asp Gly Gly Lys Val Pro Ile Lys Trp Met Ala Leu Glu Ser Ile Leu
            885                  890                  895

Arg Arg Arg Phe Thr His Gln Ser Asp Val Trp Ser Tyr Gly Val Thr
            900                  905                  910

Val Trp Glu Leu Met Thr Phe Gly Ala Lys Pro Tyr Asp Gly Ile Pro
            915                  920                  925

Ala Arg Glu Ile Pro Asp Leu Leu Glu Lys Gly Glu Arg Leu Pro Gln
    930                  935                  940

Pro Pro Ile Cys Thr Ile Asp Val Tyr Met Ile Met Val Lys Cys Trp
945                  950                  955                  960

Met Ile Asp Ser Glu Cys Arg Pro Arg Phe Arg Glu Leu Val Ser Glu
            965                  970                  975

Phe Ser Arg Met Ala Arg Asp Pro Gln Arg Phe Val Val Ile Gln Asn
            980                  985                  990

Glu Asp Leu Gly Pro Ser Ser Pro  Met Asp Ser Thr Phe  Tyr Arg Ser
            995                  1000                  1005

Leu Leu  Glu Asp Asp Asp Met  Gly Glu Leu Val Asp  Ala Glu Glu
    1010                  1015                  1020

Tyr Leu  Val Pro Gln Gln Gly  Phe Phe Ser Pro Asp  Pro Ala Leu
    1025                  1030                  1035

Gly Thr  Gly Ser Thr Ala His  Arg Arg His Arg Ser  Ser Ser Ala
    1040                  1045                  1050

Arg Ser  Gly Gly Gly Glu Leu  Thr Leu Gly Leu Glu  Pro Ser Glu
    1055                  1060                  1065

Glu Glu  Pro Pro Arg Ser Pro  Leu Ala Pro Ser Glu  Gly Ala Gly
    1070                  1075                  1080

Ser Asp  Val Phe Asp Gly Asp  Leu Ala Val Gly Val  Thr Lys Gly
    1085                  1090                  1095

Leu Gln  Ser Leu Ser Pro His  Asp Leu Ser Pro Leu  Gln Arg Tyr
    1100                  1105                  1110

Ser Glu  Asp Pro Thr Leu Pro  Leu Pro Pro Glu Thr  Asp Gly Tyr
    1115                  1120                  1125

Val Ala  Pro Leu Ala Cys Ser  Pro Gln Pro Glu Tyr  Val Asn Gln
    1130                  1135                  1140

Pro Glu  Val Arg Pro Gln Ser  Pro Leu Thr Pro Glu  Gly Pro Pro
    1145                  1150                  1155

Pro Pro  Ile Arg Pro Ala Gly  Ala Thr Leu Glu Arg  Pro Lys Thr
    1160                  1165                  1170

Leu Ser  Pro Gly Lys Asn Gly  Val Val Lys Asp Val  Phe Ala Phe
    1175                  1180                  1185

Gly Gly  Ala Val Glu Asn Pro  Glu Tyr Leu Ala Pro  Arg Ala Gly
    1190                  1195                  1200

Thr Ala  Ser Gln Pro His Pro  Ser Pro Ala Phe Ser  Pro Ala Phe
    1205                  1210                  1215
```

-continued

```
Asp Asn  Leu Tyr Tyr Trp Asp  Gln Asn Ser Ser Glu  Gln Gly Pro
    1220            1225            1230

Pro Pro  Ser Thr Phe Glu Gly  Thr Pro Thr Ala Glu  Asn Pro Glu
    1235            1240            1245

Tyr Leu  Gly Leu Asp Val Pro  Val
    1250            1255

<210> SEQ ID NO 12
<211> LENGTH: 1259
<212> TYPE: PRT
<213> ORGANISM: Rattus norvegicus

<400> SEQUENCE: 12

Met Ile Ile Met Glu Leu Ala Ala Trp Cys Arg Trp Gly Phe Leu Leu
1               5                   10                  15

Ala Leu Leu Pro Pro Gly Ile Ala Gly Thr Gln Val Cys Thr Gly Thr
            20                  25                  30

Asp Met Lys Leu Arg Leu Pro Ala Ser Pro Glu Thr His Leu Asp Met
        35                  40                  45

Leu Arg His Leu Tyr Gln Gly Cys Gln Val Val Gln Gly Asn Leu Glu
    50                  55                  60

Leu Thr Tyr Val Pro Ala Asn Ala Ser Leu Ser Phe Leu Gln Asp Ile
65                  70                  75                  80

Gln Glu Val Gln Gly Tyr Met Leu Ile Ala His Asn Gln Val Lys Arg
                85                  90                  95

Val Pro Leu Gln Arg Leu Arg Ile Val Arg Gly Thr Gln Leu Phe Glu
            100                 105                 110

Asp Lys Tyr Ala Leu Ala Val Leu Asp Asn Arg Asp Pro Gln Asp Asn
        115                 120                 125

Val Ala Ala Ser Thr Pro Gly Arg Thr Pro Glu Gly Leu Arg Glu Leu
    130                 135                 140

Gln Leu Arg Ser Leu Thr Glu Ile Leu Lys Gly Gly Val Leu Ile Arg
145                 150                 155                 160

Gly Asn Pro Gln Leu Cys Tyr Gln Asp Met Val Leu Trp Lys Asp Val
            165                 170                 175

Phe Arg Lys Asn Asn Gln Leu Ala Pro Val Asp Ile Asp Thr Asn Arg
            180                 185                 190

Ser Arg Ala Cys Pro Pro Cys Ala Pro Ala Cys Lys Asp Asn His Cys
        195                 200                 205

Trp Gly Glu Ser Pro Glu Asp Cys Gln Ile Leu Thr Gly Thr Ile Cys
    210                 215                 220

Thr Ser Gly Cys Ala Arg Cys Lys Gly Arg Leu Pro Thr Asp Cys Cys
225                 230                 235                 240

His Glu Gln Cys Ala Ala Gly Cys Thr Gly Pro Lys His Ser Asp Cys
            245                 250                 255

Leu Ala Cys Leu His Phe Asn His Ser Gly Ile Cys Glu Leu His Cys
            260                 265                 270

Pro Ala Leu Val Thr Tyr Asn Thr Asp Thr Phe Glu Ser Met His Asn
        275                 280                 285

Pro Glu Gly Arg Tyr Thr Phe Gly Ala Ser Cys Val Thr Thr Cys Pro
    290                 295                 300

Tyr Asn Tyr Leu Ser Thr Glu Val Gly Ser Cys Thr Leu Val Cys Pro
305                 310                 315                 320

Pro Asn Asn Gln Glu Val Thr Ala Glu Asp Gly Thr Gln Arg Cys Glu
```

-continued

```
                325              330              335

Lys Cys Ser Lys Pro Cys Ala Arg Val Cys Tyr Gly Leu Gly Met Glu
            340              345              350

His Leu Arg Gly Ala Arg Ala Ile Thr Ser Asp Asn Val Gln Glu Phe
            355              360              365

Asp Gly Cys Lys Lys Ile Phe Gly Ser Leu Ala Phe Leu Pro Glu Ser
            370              375              380

Phe Asp Gly Asp Pro Ser Ser Gly Ile Ala Pro Leu Arg Pro Glu Gln
385              390              395              400

Leu Gln Val Phe Glu Thr Leu Glu Glu Ile Thr Gly Tyr Leu Tyr Ile
                405              410              415

Ser Ala Trp Pro Asp Ser Leu Arg Asp Leu Ser Val Phe Gln Asn Leu
            420              425              430

Arg Ile Ile Arg Gly Arg Ile Leu His Asp Gly Ala Tyr Ser Leu Thr
            435              440              445

Leu Gln Gly Leu Gly Ile His Ser Leu Gly Leu Arg Ser Leu Arg Glu
            450              455              460

Leu Gly Ser Gly Leu Ala Leu Ile His Arg Asn Ala His Leu Cys Phe
465              470              475              480

Val His Thr Val Pro Trp Asp Gln Leu Phe Arg Asn Pro His Gln Ala
                485              490              495

Leu Leu His Ser Gly Asn Arg Pro Glu Glu Asp Cys Gly Leu Glu Gly
            500              505              510

Leu Val Cys Asn Ser Leu Cys Ala His Gly His Cys Trp Gly Pro Gly
            515              520              525

Pro Thr Gln Cys Val Asn Cys Ser His Phe Leu Arg Gly Gln Glu Cys
            530              535              540

Val Glu Glu Cys Arg Val Trp Lys Gly Leu Pro Arg Glu Tyr Val Ser
545              550              555              560

Asp Lys Arg Cys Leu Pro Cys His Pro Glu Cys Gln Pro Gln Asn Ser
            565              570              575

Ser Glu Thr Cys Phe Gly Ser Glu Ala Asp Gln Cys Ala Ala Cys Ala
            580              585              590

His Tyr Lys Asp Ser Ser Ser Cys Val Ala Arg Cys Pro Ser Gly Val
            595              600              605

Lys Pro Asp Leu Ser Tyr Met Pro Ile Trp Lys Tyr Pro Asp Glu Glu
            610              615              620

Gly Ile Cys Gln Pro Cys Pro Ile Asn Cys Thr His Ser Cys Val Asp
625              630              635              640

Leu Asp Glu Arg Gly Cys Pro Ala Glu Gln Arg Ala Ser Pro Val Thr
            645              650              655

Phe Ile Ile Ala Thr Val Val Gly Val Leu Leu Phe Leu Ile Leu Val
            660              665              670

Val Val Val Gly Ile Leu Ile Lys Arg Arg Arg Gln Lys Ile Arg Lys
            675              680              685

Tyr Thr Met Arg Arg Leu Leu Gln Glu Thr Glu Leu Val Glu Pro Leu
            690              695              700

Thr Pro Ser Gly Ala Met Pro Asn Gln Ala Gln Met Arg Ile Leu Lys
705              710              715              720

Glu Thr Glu Leu Arg Lys Val Lys Val Leu Gly Ser Gly Ala Phe Gly
            725              730              735

Thr Val Tyr Lys Gly Ile Trp Ile Pro Asp Gly Glu Asn Val Lys Ile
            740              745              750
```

-continued

```
Pro Val Ala Ile Lys Val Leu Arg Glu Asn Thr Ser Pro Lys Ala Asn
        755             760             765

Lys Glu Ile Leu Asp Glu Ala Tyr Val Met Ala Gly Val Gly Ser Pro
    770             775             780

Tyr Val Ser Arg Leu Leu Gly Ile Cys Leu Thr Ser Thr Val Gln Leu
785             790             795             800

Val Thr Gln Leu Met Pro Tyr Gly Cys Leu Leu Asp His Val Arg Glu
            805             810             815

His Arg Gly Arg Leu Gly Ser Gln Asp Leu Leu Asn Trp Cys Val Gln
            820             825             830

Ile Ala Lys Gly Met Ser Tyr Leu Glu Asp Val Arg Leu Val His Arg
        835             840             845

Asp Leu Ala Ala Arg Asn Val Leu Val Lys Ser Pro Asn His Val Lys
    850             855             860

Ile Thr Asp Phe Gly Leu Ala Arg Leu Leu Asp Ile Asp Glu Thr Glu
865             870             875             880

Tyr His Ala Asp Gly Gly Lys Val Pro Ile Lys Trp Met Ala Leu Glu
            885             890             895

Ser Ile Leu Arg Arg Arg Phe Thr His Gln Ser Asp Val Trp Ser Tyr
        900             905             910

Gly Val Thr Val Trp Glu Leu Met Thr Phe Gly Ala Lys Pro Tyr Asp
        915             920             925

Gly Ile Pro Ala Arg Glu Ile Pro Asp Leu Leu Glu Lys Gly Glu Arg
    930             935             940

Leu Pro Gln Pro Pro Ile Cys Thr Ile Asp Val Tyr Met Ile Met Val
945             950             955             960

Lys Cys Trp Met Ile Asp Ser Glu Cys Arg Pro Arg Phe Arg Glu Leu
            965             970             975

Val Ser Glu Phe Ser Arg Met Ala Arg Asp Pro Gln Arg Phe Val Val
            980             985             990

Ile Gln Asn Glu Asp Leu Gly Pro  Ser Ser Pro Met Asp  Ser Thr Phe
        995             1000            1005

Tyr Arg  Ser Leu Leu Glu Asp  Asp Asp Met Gly Asp  Leu Val Asp
    1010            1015            1020

Ala Glu  Glu Tyr Leu Val Pro  Gln Gln Gly Phe Phe  Ser Pro Asp
    1025            1030            1035

Pro Thr  Pro Gly Thr Gly Ser  Thr Ala His Arg Arg  His Arg Ser
    1040            1045            1050

Ser Ser  Thr Arg Ser Gly Gly  Gly Glu Leu Thr Leu  Gly Leu Glu
    1055            1060            1065

Pro Ser  Glu Glu Gly Pro Pro  Arg Ser Pro Leu Ala  Pro Ser Glu
    1070            1075            1080

Gly Ala  Gly Ser Asp Val Phe  Asp Gly Asp Leu Ala  Met Gly Val
    1085            1090            1095

Thr Lys  Gly Leu Gln Ser Leu  Ser Pro His Asp Leu  Ser Pro Leu
    1100            1105            1110

Gln Arg  Tyr Ser Glu Asp Pro  Thr Leu Pro Leu Pro  Pro Glu Thr
    1115            1120            1125

Asp Gly  Tyr Val Ala Pro Leu  Ala Cys Ser Pro Gln  Pro Glu Tyr
    1130            1135            1140

Val Asn  Gln Ser Glu Val Gln  Pro Gln Pro Pro Leu  Thr Pro Glu
    1145            1150            1155
```

```
Gly Pro  Leu Pro Pro Val Arg  Pro Ala Gly Ala Thr  Leu Glu Arg
    1160             1165             1170

Pro Lys  Thr Leu Ser Pro Gly  Lys Asn Gly Val Val  Lys Asp Val
    1175             1180             1185

Phe Ala  Phe Gly Gly Ala Val  Glu Asn Pro Glu Tyr  Leu Val Pro
    1190             1195             1200

Arg Glu  Gly Thr Ala Ser Pro  Pro His Pro Ser Pro  Ala Phe Ser
    1205             1210             1215

Pro Ala  Phe Asp Asn Leu Tyr  Tyr Trp Asp Gln Asn  Ser Ser Glu
    1220             1225             1230

Gln Gly  Pro Pro Pro Ser Asn  Phe Glu Gly Thr Pro  Thr Ala Glu
    1235             1240             1245

Asn Pro  Glu Tyr Leu Gly Leu  Asp Val Pro Val
    1250             1255
```

```
<210> SEQ ID NO 13
<211> LENGTH: 1091
<212> TYPE: PRT
<213> ORGANISM: Homo sapiens

<400> SEQUENCE: 13
```

```
Met Arg Pro Ser Gly Thr Ala Gly Ala Ala Leu Leu Ala Leu Leu Ala
1               5               10              15

Ala Leu Cys Pro Ala Ser Arg Ala Leu Glu Glu Lys Lys Val Cys Gln
        20              25              30

Gly Thr Ser Asn Lys Leu Thr Gln Leu Gly Thr Phe Glu Asp His Phe
        35              40              45

Leu Ser Leu Gln Arg Met Phe Asn Asn Cys Glu Val Val Leu Gly Asn
    50              55              60

Leu Glu Ile Thr Tyr Val Gln Arg Asn Tyr Asp Leu Ser Phe Leu Lys
65              70              75              80

Thr Ile Gln Glu Val Ala Gly Tyr Val Leu Ile Ala Leu Asn Thr Val
                85              90              95

Glu Arg Ile Pro Leu Glu Asn Leu Gln Ile Ile Arg Gly Asn Met Tyr
            100             105             110

Tyr Glu Asn Ser Tyr Ala Leu Ala Val Leu Ser Asn Tyr Asp Ala Asn
        115             120             125

Lys Thr Gly Leu Lys Glu Leu Pro Met Arg Asn Leu Gln Gly Gln Lys
    130             135             140

Cys Asp Pro Ser Cys Pro Asn Gly Ser Cys Trp Gly Ala Gly Glu Glu
145             150             155             160

Asn Cys Gln Lys Leu Thr Lys Ile Ile Cys Ala Gln Gln Cys Ser Gly
            165             170             175

Arg Cys Arg Gly Lys Ser Pro Ser Asp Cys Cys His Asn Gln Cys Ala
        180             185             190

Ala Gly Cys Thr Gly Pro Arg Glu Ser Asp Cys Leu Val Cys Arg Lys
        195             200             205

Phe Arg Asp Glu Ala Thr Cys Lys Asp Thr Cys Pro Pro Leu Met Leu
    210             215             220

Tyr Asn Pro Thr Thr Tyr Gln Met Asp Val Asn Pro Glu Gly Lys Tyr
225             230             235             240

Ser Phe Gly Ala Thr Cys Val Lys Lys Cys Pro Arg Asn Tyr Val Val
            245             250             255

Thr Asp His Gly Ser Cys Val Arg Ala Cys Gly Ala Asp Ser Tyr Glu
            260             265             270
```

```
Met Glu Glu Asp Gly Val Arg Lys Cys Lys Lys Cys Glu Gly Pro Cys
    275                 280                 285

Arg Lys Val Cys Asn Gly Ile Gly Ile Gly Glu Phe Lys Asp Ser Leu
    290                 295                 300

Ser Ile Asn Ala Thr Asn Ile Lys His Phe Lys Asn Cys Thr Ser Ile
305                 310                 315                 320

Ser Gly Asp Leu His Ile Leu Pro Val Ala Phe Arg Gly Asp Ser Phe
                325                 330                 335

Thr His Thr Pro Pro Leu Asp Pro Gln Glu Leu Asp Ile Leu Lys Thr
                340                 345                 350

Val Lys Glu Ile Thr Gly Phe Leu Leu Ile Gln Ala Trp Pro Glu Asn
    355                 360                 365

Arg Thr Asp Leu His Ala Phe Glu Asn Leu Glu Ile Ile Arg Gly Arg
    370                 375                 380

Thr Lys Gln His Gly Gln Phe Ser Leu Ala Val Val Ser Leu Asn Ile
385                 390                 395                 400

Thr Ser Leu Gly Leu Arg Ser Leu Lys Glu Ile Ser Asp Gly Asp Val
                405                 410                 415

Ile Ile Ser Gly Asn Lys Asn Leu Cys Tyr Ala Asn Thr Ile Asn Trp
                420                 425                 430

Lys Lys Leu Phe Gly Thr Ser Gly Gln Lys Thr Lys Ile Ile Ser Asn
                435                 440                 445

Arg Gly Glu Asn Ser Cys Lys Ala Thr Gly Gln Val Cys His Ala Leu
    450                 455                 460

Cys Ser Pro Glu Gly Cys Trp Gly Pro Glu Pro Arg Asp Cys Val Ser
465                 470                 475                 480

Cys Arg Asn Val Ser Arg Gly Arg Glu Cys Val Asp Lys Cys Asn Leu
                485                 490                 495

Leu Glu Gly Glu Pro Arg Glu Phe Val Glu Asn Ser Glu Cys Ile Gln
                500                 505                 510

Cys His Pro Glu Cys Leu Pro Gln Ala Met Asn Ile Thr Cys Thr Gly
                515                 520                 525

Arg Gly Pro Asp Asn Cys Ile Gln Cys Ala His Tyr Ile Asp Gly Pro
    530                 535                 540

His Cys Val Lys Thr Cys Pro Ala Gly Val Met Gly Glu Asn Asn Thr
545                 550                 555                 560

Leu Val Trp Lys Tyr Ala Asp Ala Gly His Val Cys His Leu Cys His
                565                 570                 575

Pro Asn Cys Thr Tyr Gly Cys Thr Gly Pro Gly Leu Glu Gly Cys Pro
                580                 585                 590

Thr Asn Gly Pro Lys Ile Pro Ser Ile Ala Thr Gly Met Val Gly Ala
                595                 600                 605

Leu Leu Leu Leu Leu Val Val Ala Leu Gly Ile Gly Leu Phe Met Arg
    610                 615                 620

Arg Arg His Ile Val Arg Lys Arg Thr Leu Arg Arg Leu Leu Gln Glu
625                 630                 635                 640

Arg Glu Leu Val Glu Pro Leu Thr Pro Ser Gly Glu Ala Pro Asn Gln
                645                 650                 655

Ala Leu Leu Arg Ile Leu Lys Glu Thr Glu Phe Lys Lys Ile Lys Val
                660                 665                 670

Leu Gly Ser Gly Ala Phe Gly Thr Val Tyr Lys Gly Leu Trp Ile Pro
                675                 680                 685
```

-continued

```
Glu Gly Glu Lys Val Lys Ile Pro Val Ala Ile Lys Glu Leu Arg Glu
    690                 695                 700

Ala Thr Ser Pro Lys Ala Asn Lys Glu Ile Leu Asp Glu Ala Tyr Val
705                 710                 715                 720

Met Ala Ser Val Asp Asn Pro His Val Cys Arg Leu Leu Gly Ile Cys
                725                 730                 735

Leu Thr Ser Thr Val Gln Leu Ile Thr Gln Leu Met Pro Phe Gly Cys
                740                 745                 750

Leu Leu Asp Tyr Val Arg Glu His Lys Asp Asn Ile Gly Ser Gln Tyr
                755                 760                 765

Leu Leu Asn Trp Cys Val Gln Ile Ala Lys Gly Met Asn Tyr Leu Glu
    770                 775                 780

Asp Arg Arg Leu Val His Arg Asp Leu Ala Ala Arg Asn Val Leu Val
785                 790                 795                 800

Lys Thr Pro Gln His Val Lys Ile Thr Asp Phe Gly Leu Ala Lys Leu
                805                 810                 815

Leu Gly Ala Glu Glu Lys Glu Tyr His Ala Glu Gly Gly Lys Val Pro
                820                 825                 830

Ile Lys Trp Met Ala Leu Glu Ser Ile Leu His Arg Ile Tyr Thr His
                835                 840                 845

Gln Ser Asp Val Trp Ser Tyr Gly Val Thr Val Trp Glu Leu Met Thr
    850                 855                 860

Phe Gly Ser Lys Pro Tyr Asp Gly Ile Pro Ala Ser Glu Ile Ser Ser
865                 870                 875                 880

Ile Leu Glu Lys Gly Glu Arg Leu Pro Gln Pro Pro Ile Cys Thr Ile
                885                 890                 895

Asp Val Tyr Met Ile Met Val Lys Cys Trp Met Ile Asp Ala Asp Ser
                900                 905                 910

Arg Pro Lys Phe Arg Glu Leu Ile Ile Glu Phe Ser Lys Met Ala Arg
    915                 920                 925

Asp Pro Gln Arg Tyr Leu Val Ile Gln Gly Asp Glu Arg Met His Leu
    930                 935                 940

Pro Ser Pro Thr Asp Ser Asn Phe Tyr Arg Ala Leu Met Asp Glu Glu
945                 950                 955                 960

Asp Met Asp Asp Val Val Asp Ala Asp Glu Tyr Leu Ile Pro Gln Gln
                965                 970                 975

Gly Phe Phe Ser Ser Pro Ser Thr Ser Arg Thr Pro Leu Leu Ser Ser
                980                 985                 990

Leu Ser Ala Thr Ser Asn Asn Ser  Thr Val Ala Cys Ile  Asp Arg Asn
    995                 1000                1005

Gly Leu  Gln Ser Cys Pro Ile  Lys Glu Asp Ser Phe  Leu Gln Arg
    1010                1015                1020

Tyr Ser  Ser Asp Pro Thr Gly  Ala Leu Thr Glu Asp  Ser Ile Asp
    1025                1030                1035

Asp Thr  Phe Leu Pro Val Pro  Gly Glu Trp Leu Val  Trp Lys Gln
    1040                1045                1050

Ser Cys  Ser Ser Thr Ser Ser  Thr His Ser Ala Ala  Ala Ser Leu
    1055                1060                1065

Gln Cys  Pro Ser Gln Val Leu  Pro Pro Ala Ser Pro  Glu Gly Glu
    1070                1075                1080

Thr Val  Ala Asp Leu Gln Thr  Gln
    1085                1090
```

-continued

```
<210> SEQ ID NO 14
<211> LENGTH: 1136
<212> TYPE: PRT
<213> ORGANISM: Homo sapiens

<400> SEQUENCE: 14

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380
```

-continued

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                    405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
        610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
        690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
        770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn

-continued

```
              805              810              815

Trp Cys Val Gln Ile Ala Lys Gly Met Asn Tyr Leu Glu Asp Arg Arg
            820              825              830

Leu Val His Arg Asp Leu Ala Ala Arg Asn Val Leu Val Lys Thr Pro
        835              840              845

Gln His Val Lys Ile Thr Asp Phe Gly Leu Ala Lys Leu Leu Gly Ala
    850              855              860

Glu Glu Lys Glu Tyr His Ala Glu Gly Gly Lys Val Pro Ile Lys Trp
865              870              875              880

Met Ala Leu Glu Ser Ile Leu His Arg Ile Tyr Thr His Gln Ser Asp
            885              890              895

Val Trp Ser Tyr Gly Val Thr Val Trp Glu Leu Met Thr Phe Gly Ser
        900              905              910

Lys Pro Tyr Asp Gly Ile Pro Ala Ser Glu Ile Ser Ser Ile Leu Glu
        915              920              925

Lys Gly Glu Arg Leu Pro Gln Pro Pro Ile Cys Thr Ile Asp Val Tyr
    930              935              940

Met Ile Met Val Lys Cys Trp Met Ile Asp Ala Asp Ser Arg Pro Lys
945              950              955              960

Phe Arg Glu Leu Ile Ile Glu Phe Ser Lys Met Ala Arg Asp Pro Gln
            965              970              975

Arg Tyr Leu Val Ile Gln Gly Asp Glu Arg Met His Leu Pro Ser Pro
        980              985              990

Thr Asp Ser Asn Phe Tyr Arg Ala  Leu Met Asp Glu Glu  Asp Met Asp
        995              1000              1005

Asp Val  Val Asp Ala Asp Glu  Tyr Leu Ile Pro Gln  Gln Gly Phe
    1010              1015              1020

Phe Ser  Ser Pro Ser Thr Ser  Arg Thr Pro Leu Leu  Ser Ser Leu
    1025              1030              1035

Ser Ala  Thr Ser Asn Asn Ser  Thr Val Ala Cys Ile  Asp Arg Asn
    1040              1045              1050

Gly Leu  Gln Ser Cys Pro Ile  Lys Glu Asp Ser Phe  Leu Gln Arg
    1055              1060              1065

Tyr Ser  Ser Asp Pro Thr Gly  Ala Leu Thr Glu Asp  Ser Ile Asp
    1070              1075              1080

Asp Thr  Phe Leu Pro Val Pro  Gly Glu Trp Leu Val  Trp Lys Gln
    1085              1090              1095

Ser Cys  Ser Ser Thr Ser Ser  Thr His Ser Ala Ala  Ala Ser Leu
    1100              1105              1110

Gln Cys  Pro Ser Gln Val Leu  Pro Pro Ala Ser Pro  Glu Gly Glu
    1115              1120              1125

Thr Val  Ala Asp Leu Gln Thr  Gln
    1130              1135
```

```
<210> SEQ ID NO 15
<211> LENGTH: 1165
<212> TYPE: PRT
<213> ORGANISM: Homo sapiens

<400> SEQUENCE: 15

Met Arg Pro Ser Gly Thr Ala Gly Ala Ala Leu Leu Ala Leu Leu Ala
1               5               10              15

Ala Leu Cys Pro Ala Ser Arg Ala Leu Glu Glu Lys Lys Val Cys Gln
        20              25              30
```

```
Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Gly Gln Lys
    130                 135                 140

Cys Asp Pro Ser Cys Pro Asn Gly Ser Cys Trp Gly Ala Gly Glu Glu
145                 150                 155                 160

Asn Cys Gln Lys Leu Thr Lys Ile Ile Cys Ala Gln Gln Cys Ser Gly
                165                 170                 175

Arg Cys Arg Gly Lys Ser Pro Ser Asp Cys Cys His Asn Gln Cys Ala
            180                 185                 190

Ala Gly Cys Thr Gly Pro Arg Glu Ser Asp Cys Leu Val Cys Arg Lys
            195                 200                 205

Phe Arg Asp Glu Ala Thr Cys Lys Asp Thr Cys Pro Pro Leu Met Leu
        210                 215                 220

Tyr Asn Pro Thr Thr Tyr Gln Met Asp Val Asn Pro Glu Gly Lys Tyr
225                 230                 235                 240

Ser Phe Gly Ala Thr Cys Val Lys Lys Cys Pro Arg Asn Tyr Val Val
                245                 250                 255

Thr Asp His Gly Ser Cys Val Arg Ala Cys Gly Ala Asp Ser Tyr Glu
            260                 265                 270

Met Glu Glu Asp Gly Val Arg Lys Cys Lys Lys Cys Glu Gly Pro Cys
        275                 280                 285

Arg Lys Val Cys Asn Gly Ile Gly Ile Gly Glu Phe Lys Asp Ser Leu
    290                 295                 300

Ser Ile Asn Ala Thr Asn Ile Lys His Phe Lys Asn Cys Thr Ser Ile
305                 310                 315                 320

Ser Gly Asp Leu His Ile Leu Pro Val Ala Phe Arg Gly Asp Ser Phe
                325                 330                 335

Thr His Thr Pro Pro Leu Asp Pro Gln Glu Leu Asp Ile Leu Lys Thr
            340                 345                 350

Val Lys Glu Ile Thr Gly Phe Leu Leu Ile Gln Ala Trp Pro Glu Asn
        355                 360                 365

Arg Thr Asp Leu His Ala Phe Glu Asn Leu Glu Ile Ile Arg Gly Arg
    370                 375                 380

Thr Lys Gln His Gly Gln Phe Ser Leu Ala Val Val Ser Leu Asn Ile
385                 390                 395                 400

Thr Ser Leu Gly Leu Arg Ser Leu Lys Glu Ile Ser Asp Gly Asp Val
                405                 410                 415

Ile Ile Ser Gly Asn Lys Asn Leu Cys Tyr Ala Asn Thr Ile Asn Trp
                420                 425                 430

Lys Lys Leu Phe Gly Thr Ser Gly Gln Lys Thr Lys Ile Ile Ser Asn
        435                 440                 445

Arg Gly Glu Asn Ser Cys Lys Ala Thr Gly Gln Val Cys His Ala Leu
```

-continued

```
        450              455                460

Cys Ser Pro Glu Gly Cys Trp Gly Pro Glu Pro Arg Asp Cys Val Ser
465              470              475              480

Cys Arg Asn Val Ser Arg Gly Arg Glu Cys Val Asp Lys Cys Asn Leu
                485              490              495

Leu Glu Gly Glu Pro Arg Glu Phe Val Glu Asn Ser Glu Cys Ile Gln
            500              505              510

Cys His Pro Glu Cys Leu Pro Gln Ala Met Asn Ile Thr Cys Thr Gly
            515              520              525

Arg Gly Pro Asp Asn Cys Ile Gln Cys Ala His Tyr Ile Asp Gly Pro
        530              535              540

His Cys Val Lys Thr Cys Pro Ala Gly Val Met Gly Glu Asn Asn Thr
545              550              555              560

Leu Val Trp Lys Tyr Ala Asp Ala Gly His Val Cys His Leu Cys His
                565              570              575

Pro Asn Cys Thr Tyr Gly Cys Thr Gly Pro Gly Leu Glu Gly Cys Pro
            580              585              590

Thr Asn Gly Pro Lys Ile Pro Ser Ile Ala Thr Gly Met Val Gly Ala
        595              600              605

Leu Leu Leu Leu Leu Val Val Ala Leu Gly Ile Gly Leu Phe Met Arg
        610              615              620

Arg Arg His Ile Val Arg Lys Arg Thr Leu Arg Arg Leu Leu Gln Glu
625              630              635              640

Arg Glu Leu Val Glu Pro Leu Thr Pro Ser Gly Glu Ala Pro Asn Gln
            645              650              655

Ala Leu Leu Arg Ile Leu Lys Glu Thr Glu Phe Lys Lys Ile Lys Val
            660              665              670

Leu Gly Ser Gly Ala Phe Gly Thr Val Tyr Lys Gly Leu Trp Ile Pro
            675              680              685

Glu Gly Glu Lys Val Lys Ile Pro Val Ala Ile Lys Glu Leu Arg Glu
        690              695              700

Ala Thr Ser Pro Lys Ala Asn Lys Glu Ile Leu Asp Glu Ala Tyr Val
705              710              715              720

Met Ala Ser Val Asp Asn Pro His Val Cys Arg Leu Leu Gly Ile Cys
                725              730              735

Leu Thr Ser Thr Val Gln Leu Ile Thr Gln Leu Met Pro Phe Gly Cys
            740              745              750

Leu Leu Asp Tyr Val Arg Glu His Lys Asp Asn Ile Gly Ser Gln Tyr
            755              760              765

Leu Leu Asn Trp Cys Val Gln Ile Ala Lys Gly Met Asn Tyr Leu Glu
        770              775              780

Asp Arg Arg Leu Val His Arg Asp Leu Ala Ala Arg Asn Val Leu Val
785              790              795              800

Lys Thr Pro Gln His Val Lys Ile Thr Asp Phe Gly Leu Ala Lys Leu
                805              810              815

Leu Gly Ala Glu Glu Lys Glu Tyr His Ala Glu Gly Gly Lys Val Pro
            820              825              830

Ile Lys Trp Met Ala Leu Glu Ser Ile Leu His Arg Ile Tyr Thr His
            835              840              845

Gln Ser Asp Val Trp Ser Tyr Gly Val Thr Val Trp Glu Leu Met Thr
        850              855              860

Phe Gly Ser Lys Pro Tyr Asp Gly Ile Pro Ala Ser Glu Ile Ser Ser
865              870              875              880
```

-continued

```
Ile Leu Glu Lys Gly Glu Arg Leu Pro Gln Pro Pro Ile Cys Thr Ile
              885                 890                 895

Asp Val Tyr Met Ile Met Val Lys Cys Trp Met Ile Asp Ala Asp Ser
             900                 905                 910

Arg Pro Lys Phe Arg Glu Leu Ile Ile Glu Phe Ser Lys Met Ala Arg
         915                 920                 925

Asp Pro Gln Arg Tyr Leu Val Ile Gln Gly Asp Glu Arg Met His Leu
         930                 935                 940

Pro Ser Pro Thr Asp Ser Asn Phe Tyr Arg Ala Leu Met Asp Glu Glu
945                 950                 955                 960

Asp Met Asp Asp Val Val Asp Ala Asp Glu Tyr Leu Ile Pro Gln Gln
             965                 970                 975

Gly Phe Phe Ser Ser Pro Ser Thr Ser Arg Thr Pro Leu Leu Ser Ser
             980                 985                 990

Leu Ser Ala Thr Ser Asn Asn Ser  Thr Val Ala Cys Ile  Asp Arg Asn
         995                 1000                1005

Gly Leu  Gln Ser Cys Pro Ile  Lys Glu Asp Ser Phe  Leu Gln Arg
    1010                1015                1020

Tyr Ser  Ser Asp Pro Thr Gly  Ala Leu Thr Glu Asp  Ser Ile Asp
    1025                1030                1035

Asp Thr  Phe Leu Pro Val Pro  Glu Tyr Ile Asn Gln  Ser Val Pro
    1040                1045                1050

Lys Arg  Pro Ala Gly Ser Val  Gln Asn Pro Val Tyr  His Asn Gln
    1055                1060                1065

Pro Leu  Asn Pro Ala Pro Ser  Arg Asp Pro His Tyr  Gln Asp Pro
    1070                1075                1080

His Ser  Thr Ala Val Gly Asn  Pro Glu Tyr Leu Asn  Thr Val Gln
    1085                1090                1095

Pro Thr  Cys Val Asn Ser Thr  Phe Asp Ser Pro Ala  His Trp Ala
    1100                1105                1110

Gln Lys  Gly Ser His Gln Ile  Ser Leu Asp Asn Pro  Asp Tyr Gln
    1115                1120                1125

Gln Asp  Phe Phe Pro Lys Glu  Ala Lys Pro Asn Gly  Ile Phe Lys
    1130                1135                1140

Gly Ser  Thr Ala Glu Asn Ala  Glu Tyr Leu Arg Val  Ala Pro Gln
    1145                1150                1155

Ser Ser  Glu Phe Ile Gly Ala
    1160                1165

<210> SEQ ID NO 16
<211> LENGTH: 1157
<212> TYPE: PRT
<213> ORGANISM: Homo sapiens

<400> SEQUENCE: 16

Met Phe Asn Asn Cys Glu Val Val Leu Gly Asn Leu Glu Ile Thr Tyr
1               5                   10                  15

Val Gln Arg Asn Tyr Asp Leu Ser Phe Leu Lys Thr Ile Gln Glu Val
             20                  25                  30

Ala Gly Tyr Val Leu Ile Ala Leu Asn Thr Val Glu Arg Ile Pro Leu
         35                  40                  45

Glu Asn Leu Gln Ile Ile Arg Gly Asn Met Tyr Tyr Glu Asn Ser Tyr
     50                  55                  60

Ala Leu Ala Val Leu Ser Asn Tyr Asp Ala Asn Lys Thr Gly Leu Lys
```

-continued

```
65                  70                  75                  80

Glu Leu Pro Met Arg Asn Leu Gln Glu Ile Leu His Gly Ala Val Arg
            85                  90                  95

Phe Ser Asn Asn Pro Ala Leu Cys Asn Val Glu Ser Ile Gln Trp Arg
            100                 105                 110

Asp Ile Val Ser Ser Asp Phe Leu Ser Asn Met Ser Met Asp Phe Gln
            115                 120                 125

Asn His Leu Gly Ser Cys Gln Lys Cys Asp Pro Ser Cys Pro Asn Gly
        130                 135                 140

Ser Cys Trp Gly Ala Gly Glu Glu Asn Cys Gln Lys Leu Thr Lys Ile
145                 150                 155                 160

Ile Cys Ala Gln Gln Cys Ser Gly Arg Cys Arg Gly Lys Ser Pro Ser
                165                 170                 175

Asp Cys Cys His Asn Gln Cys Ala Ala Gly Cys Thr Gly Pro Arg Glu
            180                 185                 190

Ser Asp Cys Leu Val Cys Arg Lys Phe Arg Asp Glu Ala Thr Cys Lys
            195                 200                 205

Asp Thr Cys Pro Pro Leu Met Leu Tyr Asn Pro Thr Thr Tyr Gln Met
        210                 215                 220

Asp Val Asn Pro Glu Gly Lys Tyr Ser Phe Gly Ala Thr Cys Val Lys
225                 230                 235                 240

Lys Cys Pro Arg Asn Tyr Val Val Thr Asp His Gly Ser Cys Val Arg
                245                 250                 255

Ala Cys Gly Ala Asp Ser Tyr Glu Met Glu Glu Asp Gly Val Arg Lys
            260                 265                 270

Cys Lys Lys Cys Glu Gly Pro Cys Arg Lys Val Cys Asn Gly Ile Gly
            275                 280                 285

Ile Gly Glu Phe Lys Asp Ser Leu Ser Ile Asn Ala Thr Asn Ile Lys
        290                 295                 300

His Phe Lys Asn Cys Thr Ser Ile Ser Gly Asp Leu His Ile Leu Pro
305                 310                 315                 320

Val Ala Phe Arg Gly Asp Ser Phe Thr His Thr Pro Pro Leu Asp Pro
                325                 330                 335

Gln Glu Leu Asp Ile Leu Lys Thr Val Lys Glu Ile Thr Gly Phe Leu
            340                 345                 350

Leu Ile Gln Ala Trp Pro Glu Asn Arg Thr Asp Leu His Ala Phe Glu
            355                 360                 365

Asn Leu Glu Ile Ile Arg Gly Arg Thr Lys Gln His Gly Gln Phe Ser
        370                 375                 380

Leu Ala Val Val Ser Leu Asn Ile Thr Ser Leu Gly Leu Arg Ser Leu
385                 390                 395                 400

Lys Glu Ile Ser Asp Gly Asp Val Ile Ile Ser Gly Asn Lys Asn Leu
                405                 410                 415

Cys Tyr Ala Asn Thr Ile Asn Trp Lys Lys Leu Phe Gly Thr Ser Gly
            420                 425                 430

Gln Lys Thr Lys Ile Ile Ser Asn Arg Gly Glu Asn Ser Cys Lys Ala
            435                 440                 445

Thr Gly Gln Val Cys His Ala Leu Cys Ser Pro Glu Gly Cys Trp Gly
        450                 455                 460

Pro Glu Pro Arg Asp Cys Val Ser Cys Arg Asn Val Ser Arg Gly Arg
465                 470                 475                 480

Glu Cys Val Asp Lys Cys Asn Leu Leu Glu Gly Glu Pro Arg Glu Phe
                485                 490                 495
```

-continued

```
Val Glu Asn Ser Glu Cys Ile Gln Cys His Pro Glu Cys Leu Pro Gln
            500                 505                 510

Ala Met Asn Ile Thr Cys Thr Gly Arg Gly Pro Asp Asn Cys Ile Gln
            515                 520                 525

Cys Ala His Tyr Ile Asp Gly Pro His Cys Val Lys Thr Cys Pro Ala
            530                 535                 540

Gly Val Met Gly Glu Asn Asn Thr Leu Val Trp Lys Tyr Ala Asp Ala
545                 550                 555                 560

Gly His Val Cys His Leu Cys His Pro Asn Cys Thr Tyr Gly Cys Thr
                565                 570                 575

Gly Pro Gly Leu Glu Gly Cys Pro Thr Asn Gly Pro Lys Ile Pro Ser
            580                 585                 590

Ile Ala Thr Gly Met Val Gly Ala Leu Leu Leu Leu Val Val Ala
            595                 600                 605

Leu Gly Ile Gly Leu Phe Met Arg Arg Arg His Ile Val Arg Lys Arg
            610                 615                 620

Thr Leu Arg Arg Leu Leu Gln Glu Arg Glu Leu Val Glu Pro Leu Thr
625                 630                 635                 640

Pro Ser Gly Glu Ala Pro Asn Gln Ala Leu Leu Arg Ile Leu Lys Glu
                645                 650                 655

Thr Glu Phe Lys Lys Ile Lys Val Leu Gly Ser Gly Ala Phe Gly Thr
                660                 665                 670

Val Tyr Lys Gly Leu Trp Ile Pro Glu Gly Glu Lys Val Lys Ile Pro
            675                 680                 685

Val Ala Ile Lys Glu Leu Arg Glu Ala Thr Ser Pro Lys Ala Asn Lys
            690                 695                 700

Glu Ile Leu Asp Glu Ala Tyr Val Met Ala Ser Val Asp Asn Pro His
705                 710                 715                 720

Val Cys Arg Leu Leu Gly Ile Cys Leu Thr Ser Thr Val Gln Leu Ile
                725                 730                 735

Thr Gln Leu Met Pro Phe Gly Cys Leu Leu Asp Tyr Val Arg Glu His
                740                 745                 750

Lys Asp Asn Ile Gly Ser Gln Tyr Leu Leu Asn Trp Cys Val Gln Ile
            755                 760                 765

Ala Lys Gly Met Asn Tyr Leu Glu Asp Arg Arg Leu Val His Arg Asp
            770                 775                 780

Leu Ala Ala Arg Asn Val Leu Val Lys Thr Pro Gln His Val Lys Ile
785                 790                 795                 800

Thr Asp Phe Gly Leu Ala Lys Leu Leu Gly Ala Glu Glu Lys Glu Tyr
                805                 810                 815

His Ala Glu Gly Gly Lys Val Pro Ile Lys Trp Met Ala Leu Glu Ser
                820                 825                 830

Ile Leu His Arg Ile Tyr Thr His Gln Ser Asp Val Trp Ser Tyr Gly
            835                 840                 845

Val Thr Val Trp Glu Leu Met Thr Phe Gly Ser Lys Pro Tyr Asp Gly
            850                 855                 860

Ile Pro Ala Ser Glu Ile Ser Ser Ile Leu Glu Lys Gly Glu Arg Leu
865                 870                 875                 880

Pro Gln Pro Pro Ile Cys Thr Ile Asp Val Tyr Met Ile Met Val Lys
                885                 890                 895

Cys Trp Met Ile Asp Ala Asp Ser Arg Pro Lys Phe Arg Glu Leu Ile
            900                 905                 910
```

```
Ile Glu Phe Ser Lys Met Ala Arg Asp Pro Gln Arg Tyr Leu Val Ile
        915                 920                 925

Gln Gly Asp Glu Arg Met His Leu Pro Ser Pro Thr Asp Ser Asn Phe
        930                 935                 940

Tyr Arg Ala Leu Met Asp Glu Glu Asp Met Asp Asp Val Val Asp Ala
945                 950                 955                 960

Asp Glu Tyr Leu Ile Pro Gln Gln Gly Phe Phe Ser Ser Pro Ser Thr
                965                 970                 975

Ser Arg Thr Pro Leu Leu Ser Ser Leu Ser Ala Thr Ser Asn Asn Ser
        980                 985                 990

Thr Val Ala Cys Ile Asp Arg Asn Gly Leu Gln Ser Cys Pro Ile Lys
        995                 1000                1005

Glu Asp Ser Phe Leu Gln Arg Tyr Ser Ser Asp Pro Thr Gly Ala
        1010                1015                1020

Leu Thr Glu Asp Ser Ile Asp Asp Thr Phe Leu Pro Val Pro Glu
        1025                1030                1035

Tyr Ile Asn Gln Ser Val Pro Lys Arg Pro Ala Gly Ser Val Gln
        1040                1045                1050

Asn Pro Val Tyr His Asn Gln Pro Leu Asn Pro Ala Pro Ser Arg
        1055                1060                1065

Asp Pro His Tyr Gln Asp Pro His Ser Thr Ala Val Gly Asn Pro
        1070                1075                1080

Glu Tyr Leu Asn Thr Val Gln Pro Thr Cys Val Asn Ser Thr Phe
        1085                1090                1095

Asp Ser Pro Ala His Trp Ala Gln Lys Gly Ser His Gln Ile Ser
        1100                1105                1110

Leu Asp Asn Pro Asp Tyr Gln Gln Asp Phe Phe Pro Lys Glu Ala
        1115                1120                1125

Lys Pro Asn Gly Ile Phe Lys Gly Ser Thr Ala Glu Asn Ala Glu
        1130                1135                1140

Tyr Leu Arg Val Ala Pro Gln Ser Ser Glu Phe Ile Gly Ala
        1145                1150                1155

<210> SEQ ID NO 17
<211> LENGTH: 943
<212> TYPE: PRT
<213> ORGANISM: Homo sapiens

<400> SEQUENCE: 17

Met Arg Pro Ser Gly Thr Ala Gly Ala Ala Leu Leu Ala Leu Leu Ala
1                   5                   10                  15

Ala Leu Cys Pro Ala Ser Arg Ala Leu Glu Glu Lys Lys Gly Asn Tyr
                20                  25                  30

Val Val Thr Asp His Gly Ser Cys Val Arg Ala Cys Gly Ala Asp Ser
                35                  40                  45

Tyr Glu Met Glu Glu Asp Gly Val Arg Lys Cys Lys Lys Cys Glu Gly
        50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
                100                 105                 110

Ser Phe Thr His Thr Pro Pro Leu Asp Pro Gln Glu Leu Asp Ile Leu
        115                 120                 125
```

```
Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
                180                 185                 190

Asp Val Ile Ile Ser Gly Asn Lys Asn Leu Cys Tyr Ala Asn Thr Ile
                195                 200                 205

Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
                260                 265                 270

Asn Leu Leu Glu Gly Glu Pro Arg Glu Phe Val Glu Asn Ser Glu Cys
                275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
                340                 345                 350

Cys His Pro Asn Cys Thr Tyr Gly Cys Thr Gly Pro Gly Leu Glu Gly
                355                 360                 365

Cys Pro Thr Asn Gly Pro Lys Ile Pro Ser Ile Ala Thr Gly Met Val
    370                 375                 380

Gly Ala Leu Leu Leu Leu Leu Val Val Ala Leu Gly Ile Gly Leu Phe
385                 390                 395                 400

Met Arg Arg Arg His Ile Val Arg Lys Arg Thr Leu Arg Arg Leu Leu
                405                 410                 415

Gln Glu Arg Glu Leu Val Glu Pro Leu Thr Pro Ser Gly Glu Ala Pro
                420                 425                 430

Asn Gln Ala Leu Leu Arg Ile Leu Lys Glu Thr Glu Phe Lys Lys Ile
                435                 440                 445

Lys Val Leu Gly Ser Gly Ala Phe Gly Thr Val Tyr Lys Gly Leu Trp
    450                 455                 460

Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
                485                 490                 495

Tyr Val Met Ala Ser Val Asp Asn Pro His Val Cys Arg Leu Leu Gly
                500                 505                 510

Ile Cys Leu Thr Ser Thr Val Gln Leu Ile Thr Gln Leu Met Pro Phe
                515                 520                 525

Gly Cys Leu Leu Asp Tyr Val Arg Glu His Lys Asp Asn Ile Gly Ser
    530                 535                 540
```

```
Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
                565                 570                 575

Leu Val Lys Thr Pro Gln His Val Lys Ile Thr Asp Phe Gly Leu Ala
                580                 585                 590

Lys Leu Leu Gly Ala Glu Glu Lys Glu Tyr His Ala Glu Gly Gly Lys
                595                 600                 605

Val Pro Ile Lys Trp Met Ala Leu Glu Ser Ile Leu His Arg Ile Tyr
        610                 615                 620

Thr His Gln Ser Asp Val Trp Ser Tyr Gly Val Thr Val Trp Glu Leu
625                 630                 635                 640

Met Thr Phe Gly Ser Lys Pro Tyr Asp Gly Ile Pro Ala Ser Glu Ile
                645                 650                 655

Ser Ser Ile Leu Glu Lys Gly Glu Arg Leu Pro Gln Pro Pro Ile Cys
                660                 665                 670

Thr Ile Asp Val Tyr Met Ile Met Val Lys Cys Trp Met Ile Asp Ala
                675                 680                 685

Asp Ser Arg Pro Lys Phe Arg Glu Leu Ile Ile Glu Phe Ser Lys Met
        690                 695                 700

Ala Arg Asp Pro Gln Arg Tyr Leu Val Ile Gln Gly Asp Glu Arg Met
705                 710                 715                 720

His Leu Pro Ser Pro Thr Asp Ser Asn Phe Tyr Arg Ala Leu Met Asp
                725                 730                 735

Glu Glu Asp Met Asp Asp Val Val Asp Ala Asp Glu Tyr Leu Ile Pro
                740                 745                 750

Gln Gln Gly Phe Phe Ser Ser Pro Ser Thr Ser Arg Thr Pro Leu Leu
                755                 760                 765

Ser Ser Leu Ser Ala Thr Ser Asn Asn Ser Thr Val Ala Cys Ile Asp
        770                 775                 780

Arg Asn Gly Leu Gln Ser Cys Pro Ile Lys Glu Asp Ser Phe Leu Gln
785                 790                 795                 800

Arg Tyr Ser Ser Asp Pro Thr Gly Ala Leu Thr Glu Asp Ser Ile Asp
                805                 810                 815

Asp Thr Phe Leu Pro Val Pro Glu Tyr Ile Asn Gln Ser Val Pro Lys
                820                 825                 830

Arg Pro Ala Gly Ser Val Gln Asn Pro Val Tyr His Asn Gln Pro Leu
                835                 840                 845

Asn Pro Ala Pro Ser Arg Asp Pro His Tyr Gln Asp Pro His Ser Thr
        850                 855                 860

Ala Val Gly Asn Pro Glu Tyr Leu Asn Thr Val Gln Pro Thr Cys Val
865                 870                 875                 880

Asn Ser Thr Phe Asp Ser Pro Ala His Trp Ala Gln Lys Gly Ser His
                885                 890                 895

Gln Ile Ser Leu Asp Asn Pro Asp Tyr Gln Gln Asp Phe Phe Pro Lys
                900                 905                 910

Glu Ala Lys Pro Asn Gly Ile Phe Lys Gly Ser Thr Ala Glu Asn Ala
                915                 920                 925

Glu Tyr Leu Arg Val Ala Pro Gln Ser Ser Glu Phe Ile Gly Ala
        930                 935                 940
```